US007951530B2

United States Patent
Mukai et al.

(10) Patent No.: US 7,951,530 B2
(45) Date of Patent: May 31, 2011

(54) CYCLIC MALTOSYLMALTOSE, CYCLIC MALTOSYMALTOSE-FORMING ENZYME, THEIR PREPARATION AND USES

(75) Inventors: Kazuhisa Mukai, Okayama (JP); Hikaru Watanabe, Okayama (JP); Tomoyuki Nishimoto, Okayama (JP); Michio Kubota, Okayama (JP); Shigeharu Fukuda, Okayama (JP); Toshio Miyake, Okayama (JP)

(73) Assignee: Kabushiki Kaisha Hayashibara Seibutsu Kagaku Kenkyujo, Okayama-Shi (JP)

( * ) Notice: Subject to any disclaimer, the term of this patent is extended or adjusted under 35 U.S.C. 154(b) by 812 days.

(21) Appl. No.: 11/941,862

(22) Filed: Nov. 16, 2007

(65) Prior Publication Data

US 2010/0015671 A1 Jan. 21, 2010

Related U.S. Application Data

(62) Division of application No. 10/569,959, filed as application No. PCT/JP2004/012282 on Aug. 26, 2004, now Pat. No. 7,309,697.

(30) Foreign Application Priority Data

Aug. 28, 2003 (JP) ................................ 2003-304964
Jun. 14, 2004 (JP) ................................ 2004-174880

(51) Int. Cl.
*G01N 33/573* (2006.01)
*C12Q 1/48* (2006.01)
*C12P 1/00* (2006.01)
*C13K 7/00* (2006.01)
*C07H 1/00* (2006.01)

(52) U.S. Cl. ................. 435/4; 435/7.4; 435/15; 435/41; 536/123.1; 536/124

(58) Field of Classification Search ............... 435/4, 7.4, 435/15, 41; 536/123, 124
See application file for complete search history.

(56) References Cited

U.S. PATENT DOCUMENTS 5,786,196 A * 7/1998 Cote et al. .................... 435/208

FOREIGN PATENT DOCUMENTS

| | | | |
|---|---|---|---|
| JP | 7-143876 | A | 6/1995 |
| JP | 7-213283 | A | 8/1995 |
| WO | WO 01/90338 | A1 | 11/2001 |
| WO | WO 02/40659 | A1 | 5/2002 |
| WO | WO 02/055708 | A1 | 7/2002 |

OTHER PUBLICATIONS

Dexter French et a., "Studies on the Schardinger Dextrins. The Preparation and Solubility Characteristics of Alpha, Beta and Gamma Dextrins[1]", vol. 71(1), pp. 353-356, Jan. 1949.

Kazuhisa Mukai; An enzymatically produced novel cyclic tetrasacchride, Cyclo-{→6)-α-D-Gicp-(1 →4)-α-D-Glcp-(1→6)-α-d-Glcp-(1→4)-α-D-Glcp(1→} (cyclic maltosyl-(1→6)-maltose), from starch; Carbohydrate Rearch, 340 (2005); pp. 1469-1474.

Kazuhisa Mukai; Purification, Characterization, and Gene Cloning of a Novel Maltosyltransferase from an *Arthrobacter globfformis* Strain That Produces and Alternating α-1,4- and α-1,6-Cyclic Tetrasaccharide from Starch; Applied and Environmental Microbiology; vol. 72, No. 2; pp. 1065-1071; Feb. 2006.

Aga et al., Production of cyclictetrasaccharide from starch using a novel enzyme system from *Bacillus globisporus* C11. J. Biosci. Bioeng., 2002, vol. 94(4): 336-342.

* cited by examiner

*Primary Examiner* — Shaojia Anna Jiang
*Assistant Examiner* — Everett White
(74) *Attorney, Agent, or Firm* — Browdy and Neimark, PLLC

(57) ABSTRACT

An object of the present invention is to provide an option of non-reducing saccharide by providing a novel non-reducing saccharide composed of glucose as constituents and to provide a novel enzyme forming the non-reducing saccharide, a method and process for producing the same, a DNA encoding the enzyme, a recombinant DNA and transformant comprising the DNA, a composition comprising the non-reducing saccharide, and uses thereof. The present invention solves the above object by providing a novel cyclic saccharide having a structure of cyclo{>6)-α-D-glucopyranosyl-(1>4)-α-D-glucopyranosyl-(1>6)-α-D-glucopyranosyl-(1>4)-α-D-glucopyranosyl-(1>}, cyclic maltosylmaltose, novel cyclic maltosylmaltose-forming enzyme, a method and process for producing the same, a DNA encoding the enzyme, a recombinant DNA and transformant comprising the DNA, a composition comprising the cyclic maltosylmaltose or a saccharide composition comprising the same, and uses thereof.

19 Claims, 8 Drawing Sheets

SEQUENCE LISTING

```
<160> NUMBER OF SEQ ID NOS: 10

<210> SEQ ID NO 1
<211> LENGTH: 5
<212> TYPE: PRT
<213> ORGANISM: Arthrobacter globiformis

<400> SEQUENCE: 1

Asp Pro Thr Thr Ser
  1             5


<210> SEQ ID NO 2
<211> LENGTH: 583
<212> TYPE: PRT
<213> ORGANISM: Arthrobacter globiformis
```

<400> SEQUENCE: 2

```
Asp Pro Thr Thr Ser Pro Gly Pro Leu Ala Glu Gly Asp Val Ile Tyr
1               5                   10                  15

Gln Val Leu Val Asp Arg Phe Glu Asp Gly Asp Pro Thr Asn Asn Asp
            20                  25                  30

Gln Gly Asp Gly Glu Tyr Asp Pro Ser Asp Leu Gly Phe Tyr His Gly
        35                  40                  45

Gly Asp Trp Ala Gly Leu Thr Asp Arg Leu Asp Tyr Ile Ala Asp Leu
    50                  55                  60

Gly Val Thr Ala Ile Trp Leu Ser Pro Val Ser Glu Gln Gln Pro Leu
65                  70                  75                  80

Ser Arg Asp Gly Leu Glu Ala Ser Tyr His Gly Tyr Phe Thr Arg Asp
                85                  90                  95

Phe Ala Thr Pro Asn Glu His Phe Gly Asp Arg Ala Glu Leu Gln Glu
            100                 105                 110

Leu Ile Asp Thr Ala His Asp Leu Gly Leu Lys Met Ile Leu Asp Val
        115                 120                 125

Val Pro Asn His Thr Ala Asp Tyr Leu Ala Gly Thr Ser Thr Thr Tyr
    130                 135                 140

Ser Pro Ser Thr Tyr Lys Pro Ala Ser Pro Leu Asp Asp Ala Ser Tyr
145                 150                 155                 160

Phe His His Ala Gly Asp Cys Leu Phe Asn Gly Leu Glu Thr Gln Thr
                165                 170                 175

Gln Ile Glu Asn Cys Asp Leu Gly Gly Leu Asp Asp Leu Asp Gln Ser
            180                 185                 190

Asn Pro Val Val Ser Ser His Leu Met Ser Thr Tyr Lys Asp Trp Val
        195                 200                 205

Asp Met Gly Phe Asp Gly Ile Arg Val Asp Ala Ala Arg Ser Val Pro
    210                 215                 220

Lys Pro Trp Leu Ala Asp Phe Glu Ala Glu Met Gly Val Pro Thr Phe
225                 230                 235                 240

Gly Glu Val Phe Val Gly Asp Val Asp Tyr Val Ser Glu Tyr Gln Asp
                245                 250                 255

Tyr Glu Trp Gly Val Leu Asp Phe Pro Tyr Phe Phe Thr Val Arg Glu
            260                 265                 270

Ala Phe Ser Ala Asp Thr Asp Met Asn Lys Leu Gly Asp Leu Phe Asp
        275                 280                 285

Gln Asp Ser Lys Tyr Ala Asn Pro Asn Arg Leu Glu Thr Phe Leu Asp
    290                 295                 300

Asn His Asp Arg Ala Arg Phe Leu Thr Trp Ala Asp Asp Asn Tyr Gln
305                 310                 315                 320

Arg Leu Arg Ser Gly Leu Thr Phe Leu Leu Thr Ser Arg Gly Val Pro
                325                 330                 335

Val Ile Tyr Tyr Gly Thr Glu Gln Ala Asp Asp Gly Asn Gly Asn Pro
            340                 345                 350

Tyr Glu Val Pro Ile Ala Asn Lys Asp Asn Arg Lys Asp Met Glu Ser
        355                 360                 365

Phe Asp Gln Asn Ser Asn Leu Tyr Lys His Ile Gln Arg Leu Thr Ala
    370                 375                 380

Ile Lys Ala Ala Tyr Pro Ala Leu Gln Val Gly Thr Gln Arg Glu Met
385                 390                 395                 400

Trp Ser Asp Thr Ser Val Tyr Gly Phe Ser Arg Arg Val Asp Ser Thr
                405                 410                 415
```

```
Gly Ala Glu Ala Met Thr Phe Ser Ser Asn Ser Trp Thr Thr Gln Thr
            420                 425                 430

Arg Thr Val Pro Leu Arg Ala Glu Ser Ser Ile Thr Val Gly Thr Thr
        435                 440                 445

Leu Thr Asn Leu Met Asn Thr Gly Asp Thr Val Thr Val Thr Ala Gly
    450                 455                 460

Gly Val Thr Gly Lys Gln Ile Thr Val Ser Leu Gly Glu His Glu Ser
465                 470                 475                 480

Lys Val Tyr Ala Pro Gly Thr Pro Val Ser Ala Tyr Ser Pro Glu Ala
                485                 490                 495

Arg Asn Thr Thr Lys Ile Arg Val His Tyr Asn Val Gly Leu Gly His
            500                 505                 510

Ser Ile Ala Ile Arg Gly Asp Glu Tyr Pro Phe Thr Trp Thr Ser Gly
        515                 520                 525

Arg Gly Ala Arg Asn Val Ala Ser Asp Val Trp Glu Phe Glu Val Glu
    530                 535                 540

Arg Ile Pro Asp Gly Glu Thr Phe Gln Phe Lys Pro Leu Ile Asp Asp
545                 550                 555                 560

Val Thr Trp Ser Thr Gly Gly Asn Phe Thr Gly Thr Gly Gly Asp Val
                565                 570                 575

Ile Asp Ile Tyr Pro Thr Phe
            580         583


<210> SEQ ID NO 3
<211> LENGTH: 1749
<212> TYPE: DNA
<213> ORGANISM: Arthrobacter globiformis

<400> SEQUENCE: 3

gaccccacca cgtcgcccgg cccgctggcc gagggcgacg tgatctacca ggtgctcgtc      60

gaccggttcg aagacggcga ccccaccaac aacgaccagg gcgacggaga gtacgatccg     120

tccgacctcg gtttctacca cggcggcgac tgggcgggcc tgacggaccg gctcgactac     180

atcgccgatc tgggtgtgac ggcgatctgg ctctcgcccg tctccgagca gcagccgctc     240

tcgcgcgacg ggctggaggc cagctaccac ggctacttca ctcgggactt cgcgacgccg     300

aacgagcatt tcggcgaccg agccgagctg caggagctga tcgacacggc gcacgatctc     360

ggactcaaga tgatcctcga cgtcgtgccg aaccacacgg ccgactacct cgcgggcaca     420

tcgacgacct attcgccgag cacctacaag ccggcgagtc cgctcgatga cgcgtcgtac     480

ttccatcacg ccggcgactg cctgttcaac gggctcgaga cgcagaccca gatcgagaac     540

tgcgacctcg gcgggctcga cgacctcgat cagtcgaacc cggtcgtctc gtcgcacctg     600

atgagcacgt acaaggactg ggtcgacatg ggcttcgacg gcatccgggt cgatgcggcg     660

cgctcggtgc cgaagccgtg gctcgccgac ttcgaagccg agatgggcgt gccgaccttc     720

ggcgaggtgt tcgtcggcga tgtcgactac gtctcggagt accaggacta cgagtggggc     780

gtgctcgact tcccctactt cttcacggtg cgcgaggcgt tctcggccga taccgacatg     840

aacaagctcg gcgacctctt cgaccaggac agcaagtacg cgaacccgaa ccggctggag     900

acgttcctcg acaaccacga tcgggcgcgg ttcctcacct gggccgatga caactatcag     960

cggctgcgct caggactgac gttcctccta acctcccggg gcgtgcccgt gatctactac    1020

ggcaccgagc aggccgacga cggcaacggc aacccctacg aggtaccgat cgcgaacaag    1080

gacaaccgca aggacatgga gagcttcgat cagaactcga acctctacaa gcacatccag    1140
```

```
cggttgaccg cgatcaaggc cgcttacccg gctctgcagg tcggcacaca gcgcgagatg   1200

tggtccgaca cctccgtcta cgggttctcg cgacgcgtcg acagcacggg tgccgaggcg   1260

atgaccttct cgtcgaactc gtggacgacg cagacgcgca cggtgccgct gcgcgccgag   1320

agctcgatca cggtcggtac gacgctgacg aacctcatga acacgggcga cacggtgacc   1380

gtgaccgccg gcggtgtcac ggggaagcag atcaccgtct ccctcggcga gcacgagagc   1440

aaggtctatg cgcccggcac cccggtatcg gcatacagcc ccgaagcgcg caacaccacg   1500

aagatccgcg tgcactacaa cgtgggcctc gggcacagca tcgcgatccg cggcgacgag   1560

tacccgttca cctggacctc cggccgaggc gcgcgcaacg tcgcgtccga cgtctgggag   1620

ttcgaggtcg agcgcatccc cgacggtgag accttccagt tcaagcctct gatcgacgac   1680

gtcacctggt cgaccggcgg caacttcacc gggacgggcg gcgacgtgat cgacatctac   1740

cccaccttc                                                           1749


<210> SEQ ID NO 4
<211> LENGTH: 9
<212> TYPE: PRT
<213> ORGANISM: Arthrobacter globiformis

<400> SEQUENCE: 4

His Ile Gln Arg Leu Thr Ala Ile Lys
  1               5


<210> SEQ ID NO 5
<211> LENGTH: 13
<212> TYPE: PRT
<213> ORGANISM: Arthrobacter globiformis

<400> SEQUENCE: 5

Asp Met Glu Ser Phe Asp Gln Asn Ser Asn Leu Tyr Lys
  1               5                  10


<210> SEQ ID NO 6
<211> LENGTH: 10
<212> TYPE: PRT
<213> ORGANISM: Arthrobacter globiformis

<400> SEQUENCE: 6

Leu Gly Asp Leu Phe Asp Gln Asp Ser Lys
  1               5                  10


<210> SEQ ID NO 7
<211> LENGTH: 27
<212> TYPE: PRT
<213> ORGANISM: Arthrobacter globiformis

<400> SEQUENCE: 7

Met Ile Leu Asp Val Val Pro Asn His Thr Ala Asp Tyr Leu Ala Gly
  1               5                  10                  15

Thr Ser Thr Thr Tyr Ser Pro Ser Thr Tyr Lys
             20                  25


<210> SEQ ID NO 8
<211> LENGTH: 20
<212> TYPE: PRT
<213> ORGANISM: Arthrobacter globiformis

<400> SEQUENCE: 8

Asp Trp Val Asp Met Gly Phe Asp Gly Ile Arg Val Asp Ala Ala Arg
  1               5                  10                  15
```

```
Ser Val Pro Lys
            20


<210> SEQ ID NO 9
<211> LENGTH: 30
<212> TYPE: PRT
<213> ORGANISM: Arthrobacter globiformis

<400> SEQUENCE: 9

Tyr Ala Asn Pro Asn Arg Leu Glu Thr Phe Leu Asp Asn His Asp Arg
  1               5                  10                  15

Ala Arg Phe Leu Thr Trp Ala Asp Asp Asn Tyr Gln Arg Leu
            20                  25                  30


<210> SEQ ID NO 10
<211> LENGTH: 4467
<212> TYPE: DNA
<213> ORGANISM: Arthrobacter globiformis

<400> SEQUENCE: 10

ggatccctga gctggatggg catggctcac gcgctcgatc tcgagggggc ggcgaaggag     60

ctggcgaccg cagccggcga ggcacctctc ctccgcccgg ccgacctcgt ctacctcggc    120

gtcgatctcg cgcagacgac ggagggagaa cggtcgcagc gggaggcgct cgggctcgct    180

gtcgtcgagc agaacgctct cgtcgccgat cctcggcgag ctgctcggac cgcacgagcc    240

cacctcgccc caggaccgtt catcgtgcac ctggacgtcg atgtgctgga cttcctcgac    300

gcacccottg ccgagaacgt gaacggccga aacagcgggc cgaccgtcga gcagctgcgg    360

gtcgcactcg ccgagcttct gcagcatccg gactgctggg cgatgtccat cggccaggtg    420

gtccccgcgc acgcggcggc cgacccgacc tccatcccgc ggctcatcgg cgccctggcc    480

gtgagctcca cgtagccgga cgtcgctcct ggagcggagc cgctccggca ggaacggcgt    540

cgcaccccgt cgagcggggg cgtcgccctc ttcgacgggg tctgcggcgc ggctacccgc    600

gcggcagcgt gagccgccac cgaccagatc tcatgcattt ggacgaactt cgccgtccaa    660

ttctctccgc gcctcaagca ggtatacatc gctcgaacgc gtcttcactg gcctgacggt    720

ccgcgatcac gtcgtgcagt gaagcatcct gccgcgaagg gtcttgatgc gcatgcagta    780

cgggagtcga atcactttca cgggcacggc cggtgtcagt acttgacaaa acgcatttat    840

acatgttgca tcgatccagt aaaccgtgca gctcgcggac cgatgcgcat ccgacaacga    900

agtcaggaga gagtc atg aga acg aca gtt cgt acc gct cgc gtc tcc gcg     951
                 Met Arg Thr Thr Val Arg Thr Ala Arg Val Ser Ala
                   1               5                  10

cgt acg ggc ctc gcg atg gga gca gcc gtc gcg ctg gcg gcc ggc gcg      999
Arg Thr Gly Leu Ala Met Gly Ala Ala Val Ala Leu Ala Ala Gly Ala
        15                  20                  25

ctc acc tgg ggc acc ggc ccc gca ccc gcg agt gcc gac ccc acc acg     1047
Leu Thr Trp Gly Thr Gly Pro Ala Pro Ala Ser Ala Asp Pro Thr Thr
     30                  35                  40

tcg ccc ggc ccg ctg gcc gag ggc gac gtg atc tac cag gtg ctc gtc     1095
Ser Pro Gly Pro Leu Ala Glu Gly Asp Val Ile Tyr Gln Val Leu Val
 45                  50                  55                  60

gac cgg ttc gaa gac ggc gac ccc acc aac aac gac cag ggc gac gga     1143
Asp Arg Phe Glu Asp Gly Asp Pro Thr Asn Asn Asp Gln Gly Asp Gly
                 65                  70                  75

gag tac gat ccg tcc gac ctc ggt ttc tac cac ggc ggc gac tgg gcg     1191
Glu Tyr Asp Pro Ser Asp Leu Gly Phe Tyr His Gly Gly Asp Trp Ala
            80                  85                  90

ggc ctg acg gac cgg ctc gac tac atc gcc gat ctg ggt gtg acg gcg     1239
```

```
Gly Leu Thr Asp Arg Leu Asp Tyr Ile Ala Asp Leu Gly Val Thr Ala
        95                  100                 105

atc tgg ctc tcg ccc gtc tcc gag cag cag ccg ctc tcg cgc gac ggg     1287
Ile Trp Leu Ser Pro Val Ser Glu Gln Gln Pro Leu Ser Arg Asp Gly
    110                 115                 120

ctg gag gcc agc tac cac ggc tac ttc act cgg gac ttc gcg acg ccg     1335
Leu Glu Ala Ser Tyr His Gly Tyr Phe Thr Arg Asp Phe Ala Thr Pro
125                 130                 135                 140

aac gag cat ttc ggc gac cga gcc gag ctg cag gag ctg atc gac acg     1383
Asn Glu His Phe Gly Asp Arg Ala Glu Leu Gln Glu Leu Ile Asp Thr
                145                 150                 155

gcg cac gat ctc gga ctc aag atg atc ctc gac gtc gtg ccg aac cac     1431
Ala His Asp Leu Gly Leu Lys Met Ile Leu Asp Val Val Pro Asn His
            160                 165                 170

acg gcc gac tac ctc gcg ggc aca tcg acg acc tat tcg ccg agc acc     1479
Thr Ala Asp Tyr Leu Ala Gly Thr Ser Thr Thr Tyr Ser Pro Ser Thr
        175                 180                 185

tac aag ccg gcg agt ccg ctc gat gac gcg tcg tac ttc cat cac gcc     1527
Tyr Lys Pro Ala Ser Pro Leu Asp Asp Ala Ser Tyr Phe His His Ala
    190                 195                 200

ggc gac tgc ctg ttc aac ggg ctc gag acg cag acc cag atc gag aac     1575
Gly Asp Cys Leu Phe Asn Gly Leu Glu Thr Gln Thr Gln Ile Glu Asn
205                 210                 215                 220

tgc gac ctc ggc ggg ctc gac gac ctc gat cag tcg aac ccg gtc gtc     1623
Cys Asp Leu Gly Gly Leu Asp Asp Leu Asp Gln Ser Asn Pro Val Val
                225                 230                 235

tcg tcg cac ctg atg agc acg tac aag gac tgg gtc gac atg ggc ttc     1671
Ser Ser His Leu Met Ser Thr Tyr Lys Asp Trp Val Asp Met Gly Phe
            240                 245                 250

gac ggc atc cgg gtc gat gcg gcg cgc tcg gtg ccg aag ccg tgg ctc     1719
Asp Gly Ile Arg Val Asp Ala Ala Arg Ser Val Pro Lys Pro Trp Leu
        255                 260                 265

gcc gac ttc gaa gcc gag atg ggc gtg ccg acc ttc ggc gag gtg ttc     1767
Ala Asp Phe Glu Ala Glu Met Gly Val Pro Thr Phe Gly Glu Val Phe
    270                 275                 280

gtc ggc gat gtc gac tac gtc tcg gag tac cag gac tac gag tgg ggc     1815
Val Gly Asp Val Asp Tyr Val Ser Glu Tyr Gln Asp Tyr Glu Trp Gly
285                 290                 295                 300

gtg ctc gac ttc ccc tac ttc ttc acg gtg cgc gag gcg ttc tcg gcc     1863
Val Leu Asp Phe Pro Tyr Phe Phe Thr Val Arg Glu Ala Phe Ser Ala
                305                 310                 315

gat acc gac atg aac aag ctc ggc gac ctc ttc gac cag gac agc aag     1911
Asp Thr Asp Met Asn Lys Leu Gly Asp Leu Phe Asp Gln Asp Ser Lys
            320                 325                 330

tac gcg aac ccg aac cgg ctg gag acg ttc ctc gac aac cac gat cgg     1959
Tyr Ala Asn Pro Asn Arg Leu Glu Thr Phe Leu Asp Asn His Asp Arg
        335                 340                 345

gcg cgg ttc ctc acc tgg gcc gat gac aac tat cag cgg ctg cgc tca     2007
Ala Arg Phe Leu Thr Trp Ala Asp Asp Asn Tyr Gln Arg Leu Arg Ser
    350                 355                 360

gga ctg acg ttc ctc cta acc tcc cgg ggc gtg ccc gtg atc tac tac     2055
Gly Leu Thr Phe Leu Leu Thr Ser Arg Gly Val Pro Val Ile Tyr Tyr
365                 370                 375                 380

ggc acc gag cag gcc gac gac ggc aac ggc aac ccc tac gag gta ccg     2103
Gly Thr Glu Gln Ala Asp Asp Gly Asn Gly Asn Pro Tyr Glu Val Pro
                385                 390                 395

atc gcg aac aag gac aac cgc aag gac atg gag agc ttc gat cag aac     2151
Ile Ala Asn Lys Asp Asn Arg Lys Asp Met Glu Ser Phe Asp Gln Asn
            400                 405                 410

tcg aac ctc tac aag cac atc cag cgg ttg acc gcg atc aag gcc gct     2199
```

```
Ser Asn Leu Tyr Lys His Ile Gln Arg Leu Thr Ala Ile Lys Ala Ala
        415                 420                 425

tac ccg gct ctg cag gtc ggc aca cag cgc gag atg tgg tcc gac acc      2247
Tyr Pro Ala Leu Gln Val Gly Thr Gln Arg Glu Met Trp Ser Asp Thr
    430                 435                 440

tcc gtc tac ggg ttc tcg cga cgc gtc gac agc acg ggt gcc gag gcg      2295
Ser Val Tyr Gly Phe Ser Arg Arg Val Asp Ser Thr Gly Ala Glu Ala
445                 450                 455                 460

atg acc ttc tcg tcg aac tcg tgg acg acg cag acg cgc acg gtg ccg      2343
Met Thr Phe Ser Ser Asn Ser Trp Thr Thr Gln Thr Arg Thr Val Pro
                465                 470                 475

ctg cgc gcc gag agc tcg atc acg gtc ggt acg acg ctg acg aac ctc      2391
Leu Arg Ala Glu Ser Ser Ile Thr Val Gly Thr Thr Leu Thr Asn Leu
            480                 485                 490

atg aac acg ggc gac acg gtg acc gtg acc gcc ggc ggt gtc acg ggg      2439
Met Asn Thr Gly Asp Thr Val Thr Val Thr Ala Gly Gly Val Thr Gly
        495                 500                 505

aag cag atc acc gtc tcc ctc ggc gag cac gag agc aag gtc tat gcg      2487
Lys Gln Ile Thr Val Ser Leu Gly Glu His Glu Ser Lys Val Tyr Ala
    510                 515                 520

ccc ggc acc ccg gta tcg gca tac agc ccc gaa gcg cgc aac acc acg      2535
Pro Gly Thr Pro Val Ser Ala Tyr Ser Pro Glu Ala Arg Asn Thr Thr
525                 530                 535                 540

aag atc cgc gtg cac tac aac gtg ggc ctc ggg cac agc atc gcg atc      2583
Lys Ile Arg Val His Tyr Asn Val Gly Leu Gly His Ser Ile Ala Ile
                545                 550                 555

cgc ggc gac gag tac ccg ttc acc tgg acc tcc ggc cga ggc gcg cgc      2631
Arg Gly Asp Glu Tyr Pro Phe Thr Trp Thr Ser Gly Arg Gly Ala Arg
            560                 565                 570

aac gtc gcg tcc gac gtc tgg gag ttc gag gtc gag cgc atc ccc gac      2679
Asn Val Ala Ser Asp Val Trp Glu Phe Glu Val Glu Arg Ile Pro Asp
        575                 580                 585

ggt gag acc ttc cag ttc aag cct ctg atc gac gac gtc acc tgg tcg      2727
Gly Glu Thr Phe Gln Phe Lys Pro Leu Ile Asp Asp Val Thr Trp Ser
    590                 595                 600

acc ggc ggc aac ttc acc ggg acg ggc ggc gac gtg atc gac atc tac      2775
Thr Gly Gly Asn Phe Thr Gly Thr Gly Gly Asp Val Ile Asp Ile Tyr
605                 610                 615                 620

ccc acc ttc tga acccatccct cccgggactc caccgaaagg atgcttgtga gccac    2832
Pro Thr Phe

accatcgaac ggccctctcg cctcgacacg gcaaggcgcg ccttctcctg gcgcgacgcg    2892

gtcgtctacc aggtctacct gcggtcgttc cgcgacgcga acggcgacgg catcggcgac    2952

ctcggcggcc tgagccaggg tctcgacgcg atcgccgcac tcggctgcga cgccatctgg    3012

ctgaacccct gctacgcctc gccccagcgc gaccacgggt acgacatcgc cgactacctg    3072

acgatcgatc cggcgtacgg caccctcgag gagttcgacg aggtggttcg ccgagcgcac    3132

gagctcgggc tgcgcgttct gatggacatg gtcgcgaacc actgctcgtc cgaccacgcc    3192

tggttccagg cggcgttggc cgccgagccc ggcagcgacg agcgggcgcg cttcatcttc    3252

cgcgacggcc tcggccccga tggcgaactg ccgccgaaca actgggacag cgtcttcgga    3312

gggctcgcct ggacccgcgt caccgagcgc gacggacgcc ccgggcagtg gtacctccac    3372

tcctttgata cgagccagcc cgacttcgat tggcggcacc ccgcggtggc cgagcacttc    3432

gagaacgtgc tgcggttctg gttcgagcgg ggagtcgacg gcttccgcat cgacgtcgcg    3492

cacggccact tcaaggacgc cgccctgccc gaccacccgg gtggccgggg gcctgacgcc    3552

ggccacaacc acggcatgtg ggaccagccc gaggtgcacg acctctatcg ctcgtggcga    3612
```

-continued

```
gcgctcggcg atgcctacga gcccgagaag tacttcgtgg gcgagatctg ggtcccctcc   3672

cccgaccggc tggccgacta cctgcgaccc gacgagctgc acaacgcctt ctcgttcgat   3732

ctgctcgtgc agccgtggaa cgccgaccgg ttccggaagg cgatcgagac cggactcgcc   3792

gtcggacgcg ggtggccggc ctggacactg gccaaccacg acgtgcatcg tgcggtcacc   3852

cgctacggcc aggagcagcc gttggatgaa gccctgccga ccgacatgat cgccgcggcg   3912

cgacgcaggg gcccggccga tctggatcgc ggtcttcgcc gtgcgcgcgc ggcagccgcc   3972

ctcgccctcg cgctcccggg gtcgatgtac ctctatcagg gcgaagaact cgggttgccc   4032

gaggttctgg atctcccgga tgctgcgcgc caagacccga tctggacccg ctcgaacggc   4092

accgagctcg gccgggacgg gtgccgcatc cccctcccct ggacgcgaga gggccgcacc   4152

ttcggattca gcgacgcggc cgccgccacg acctggctcc cgcagcccgc gtggttcggc   4212

gcgttcgccc gggcgacgca ggcggccgat cccgactcga tgctctcgct gcatcgcgat   4272

ctcctcgcca cgcgccgcac ccacctccgc ggaacggagc cgatcgtctg gctgtccccg   4332

gcaggtgccg aggtgctcgc cttccgacgc ggggacgtcg tggtcgtcac gaacttcggc   4392

tccgcaccct tcacgccgcc gtccgcctgg ggcgcgctct cgccgctcct ggcctcccag   4452

ccgctgacgg gatcc                                                    4467
```

CYCLIC MALTOSYLMALTOSE, CYCLIC MALTOSYMALTOSE-FORMING ENZYME, THEIR PREPARATION AND USES

The present application is a divisional application of U.S. application Ser. No. 10/569,959, filed Feb. 28, 2006 now U.S. Pat. No. 7,309,697, which is a U.S. National Stage of PCT/JP04/12282 filed Aug. 26, 2004; now allowed, the entire contents of each and both these applications being hereby incorporated by reference herein.

TECHNICAL FIELD

The present invention relates to a cyclic maltosylmaltose having a structure of cyclo{>6)-α-D-glucopyranosyl-1>4)-α-D-glucopyranosyl-(1>6)-α-D-glucopyranosyl-(1>4)-α-D-glucopyranosyl-(1>} (hereinafter, may be simply abbreviated as "cyclic maltosylmaltose" or "CMM" in this specification), CMM-forming enzyme, their preparation and uses; and a DNA encoding the enzyme and a recombinant DNA comprising the DNA. More particularly, the present invention relates to CMM, CMM-forming enzyme, their preparation, a microorganism producing the enzyme, a DNA encoding the enzyme, a recombinant DNA comprising the DNA, a transformant, a method and process for producing CMM by using the enzyme, and a composition comprising CMM.

BACKGROUND ART

There have been known saccharides composed of glucose molecules as constituents, for example, partial hydrolyzates, produced from starches as materials, including amyloses, amylodextrins, maltodextrins, maltooligosaccharides, and isomaltooligosaccharides. Also, these saccharides are known to have usually non-reducing ends and reducing groups at their molecular ends and to exhibit reducing power. Usually, reducing power on a dry solid basis of partial starch hydrolyzates is represented by Dextrose Equivalent (DE). Partial starch hydrolyzates with high DE values are known to have a relatively low molecular weight, relatively low viscosity, strong sweetness and reactivity, easy reactivity with amino group-containing substances such as amino acids and proteins by amino carbonyl reaction that may induce browning and unpleasant smell and easily cause deterioration. In order to improve those disadvantages, methods for decreasing or eliminating the reducing power of partial starch hydrolyzates without altering glucose residues have been required for a long time. "*Journal of American Chemical Society*, Vol. 71, 353-358 (1949)" discloses a method to produce α-, β- or γ-cyclodextrin, constructed by 6, 7 or 8 glucose molecules bound by the α-1,4 glucosidic linkage, from starch by "macerans amylase". At present, these cyclodextrins are produced on an industrial scale and are applied to various uses because of their non-reducing power, tastelessness, and clathrating abilities. Further, Japanese Patent Kokai Nos. 143,876/95 and 213,283, applied for by the same applicant as the present invention, discloses a method to convert maltooligosaccharides and partial starch hydrolyzates into trehalose, composed of two glucose molecules linked together via the α,α-1,1 linkage, by contacting a non-reducing saccharide-forming enzyme and a trehalose-releasing enzyme. At present, trehalose is produced from starch on an industrial scale and is applied to various uses because of its non-reducing power and its mild and high quality sweetness. While, International Patent Application Nos. WO 01/90338 A1, WO 02/055708 A1, and WO 02/40659 A1, applied for by the same applicant as the present invention, disclose a method to produce acyclic tetrasaccharide, having a structure of binding four glucose molecules via alternating α-1,3 and α-1,6 glucosidic linkages, i.e., cyclo{>6)-α-D-glucopyranosyl-(1>3)-α-D-glucopyranosyl-(1>6)-α-D-glucopyranosyl-(1>3)-α-D-glucopyranosyl-(1>}, from starch or partial starch hydrolyzates by contacting α-isomaltosylglucosaccharide-forming enzyme and α-isomaltosyl-transferring enzyme. The cyclic tetrasaccharide has abilities of clathrating other substances because of its cyclic structure and stabilizing volatile organic substances. Further, since the saccharide has no reducing power, it is expected that the saccharide can be used and processed without causing browning and deterioration by amino-carbonyl reaction.

As described above, α-, β- or γ-cyclodextrin having a glucose polymerization degree of 6, 7 or 8, trehalose having a glucose polymerization degree of 2, and cyclic tetrasaccharide having a structure of cyclo{>6)-α-D-glucopyranosyl-(1>3)-α-D-glucopyranosyl-1>6)-α-D-glucopyranosyl-(1>3)-α-D-glucopyranosyl-(1>}, are used in various fields on the basis of these respective advantage as non-reducing saccharides composed with glucose molecules. While, if other non-reducing saccharides distinct from the above saccharides would be provided, we would have more choice of using non-reducing saccharides, and application thereof on various uses can be expected.

DISCLOSURE OF INVENTION

An object of the present invention is to provide an option of non-reducing saccharide by providing a novel non-reducing saccharide composed of glucoses as constituents and to provide a novel enzyme forming the non-reducing saccharide, a method and process for producing them, a DNA encoding the enzyme, a recombinant DNA and transformant comprising the DNA, a composition comprising the non-reducing saccharide, and uses thereof.

To solve the above object, the present inventors have extensively screened microorganisms capable of producing a novel non-reducing saccharide-forming enzyme which forms a novel non-reducing saccharide when allowed to act on partial starch hydrolyzates. As a result, the present inventors isolated a novel microorganism of the genus *Arthrobacter*, named "M6", from a soil in Okayama-city, Okayama, Japan, and found that the microorganism produces a novel enzyme which forms a remarkable amount of a novel cyclic saccharide having a structure of cyclo{>6)-α-D-glucopyranosyl-(1>4)-α-D-glucopyranosyl-(1>6)-α-D-glucopyranosyl-1>4)-α-D-glucopyranosyl-(1>}, i.e. CMM, when allowed to act on α-1,4 glucans such as starches and partial hydrolyzates. The present inventors also revealed the properties of CMM-forming enzyme and established the process for producing the enzyme. The present inventors also established a DNA encoding the enzyme, a recombinant DNA comprising the DNA, a transformant, a method for forming CMM by the enzyme, and processes for producing CMM and a saccharide composition comprising the same by using the enzyme. Also, it was found that CMM can be easily collected by crystallizing CMM from its supersaturated aqueous solution. Further, it was found that CMM has useful characteristics of clathrating volatile substances such as methylalcohol, ethylalcohol, and acetic acid; showing no browning and deterioration by amino carbonyl reaction; having a satisfactory stability to heating and the change of pH; and having a low digestibility and low fermentability. Furthermore, it was found that a composition, comprising CMM or a saccharide composition comprising the same, for example, foods and beverages with a high quality and a satisfactory flavor, low calorie foods and dietary foods, cosmetics with high quality and stability, pharmaceuticals with high activity and stability, etc., can be easily produced. The present invention was accomplished based on the above knowledge.

The present invention solves the above object by providing a novel cyclic saccharide having a structure of cyclo{>6)-α-D-glucopyranosyl-(1>4)-α-D-glucopyranosyl-(1>6)-α-D-glucopyranosyl-(1>4)-α-D-glucopyranosyl-(1>}, i.e. cyclic maltosylmaltose, a novel cyclic maltosylmaltose-forming enzyme, a method and process for producing them, a DNA encoding the enzyme, a recombinant DNA and transformant comprising the DNA, a composition comprising the cyclic maltosylmaltose or a saccharide composition comprising the same, and uses thereof.

According to the present invention, an option of non-reducing saccharide composed of glucose as constituents can be extended. Further, the present invention enables the provision of CMM, a novel cyclic saccharide which has been ever unknown, in large scale and the use of CMM in a various fields including foods and beverages, cosmetics, and pharmaceuticals.

In the figure, a section indicated with black bold line is a DNA encoding CMM-forming enzyme of the present invention, derived from *Arthrobacter globiformis* M6 (FERM BP-8448).

Figure 10:
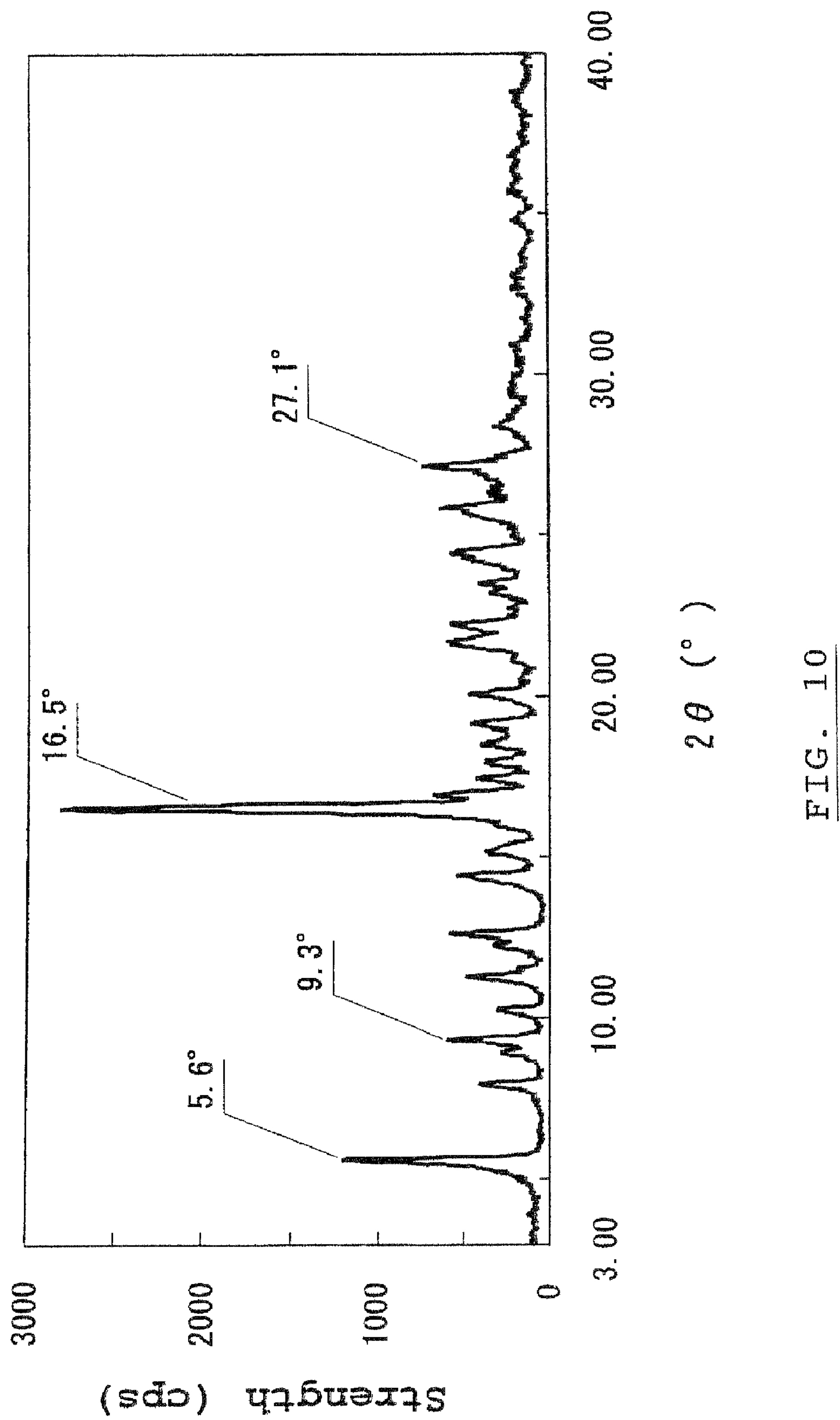

FIG. 10 shows the powdery X-ray diffraction pattern of crystalline CMM.

Figure 11:
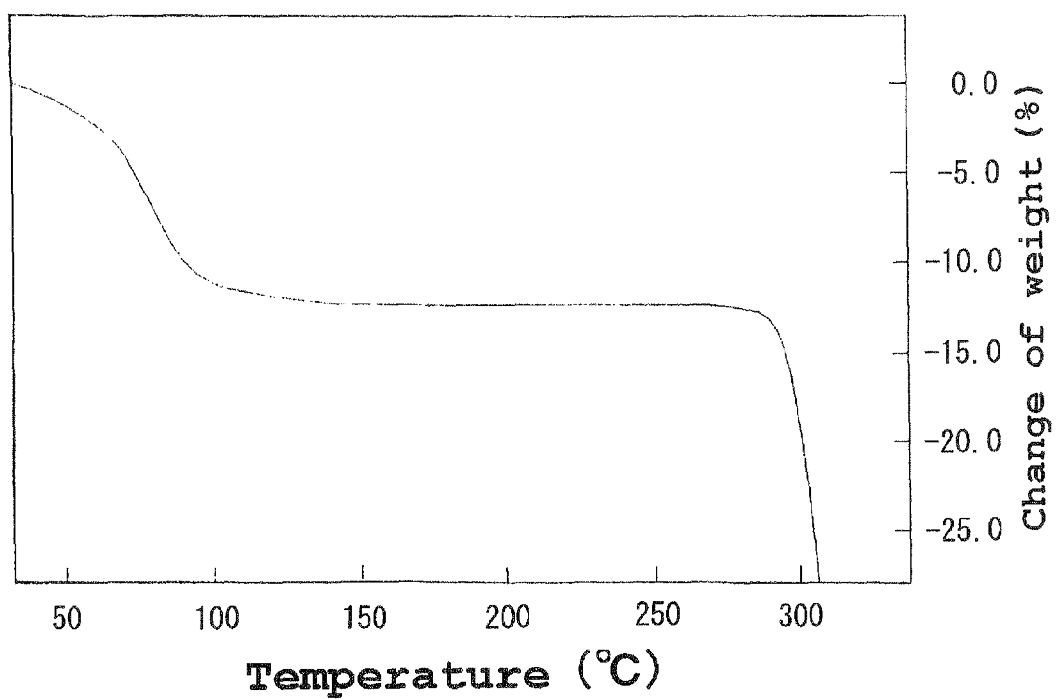

FIG. 11 shows the thermogravimetric curve of crystalline CMM.

EXPLANATION OF SYMBOLS a: Glucose residue bound via the α-1,4 glucosidic linkage by hydroxyl group at C-1 position b: Glucose residue bound via the α-1,6 glucosidic linkage by hydroxyl group at C-1 position f1 (+) ori: Replication origin of f1 phage Amp: Ampicillin resistance gene Col E1 ori: Replication origin of colicin E1

BEST MODE FOR CARRYING OUT THE INVENTION

Cyclic maltosylmaltose (CMM) as referred to as in the present invention means a cyclic tetrasaccharide where four glucose molecules are bound via alternating α-1,4 and α-1,6 glucosidic linkages, i.e. a cyclic tetrasaccharide having a structure of cyclo{>6)-α-D-glucopyranosyl-(1>4)-α-D-glucopyranosyl-(1>6)-α-D-glucopyranosyl-(1>4)-α-D-glucopyranosyl-(1>}. The saccharide is a novel and ever unknown saccharide, firstly found in a culture medium of a microorganism isolated from a soil by the present inventors. The present invention encompasses a cyclic tetrasaccharide constructed by glucose without being restricted by its source, form, purity, and process for producing, as far as it has the above mentioned structure.

CMM-forming enzyme as referred to as in the present invention means any enzyme which acts on α-1,4 glucans having a glucose polymerization degree of 3 or higher to form 6-α-maltosyl-α-1,4-glucan by transferring maltose to the C-6 position of glucose residue at the non-reducing end of other α-1,4 glucan; and successively forms CMM having a structure of cyclo{>6)-α-D-glucopyranosyl-(1>4)-α-glucopyranosyl-1>6)-α-D-glucopyranosyl-(1>4)-α-D-glucopyranosyl-(1>} by a cyclization reaction. CMM-forming enzyme of the present invention encompasses any enzyme catalyzing the above reaction without being restricted by its source, form, and purity (crude or purified).

The enzyme activity of CMM-forming enzyme of the present invention can be assayed as follows: A substrate solution is prepared by dissolving soluble starch in 50 mM acetate buffer (pH 6.0) containing 2 mM $CaCl_2$ to give a concentration of 2% (w/v). A half milliliter of an enzyme solution is added to 0.5 ml of the substrate solution, and the mixture solution is incubated at 40° C. for 30 min. After stopping the reaction by heating at about 100° C. for 10 min, the reaction mixture is admixed with 4,000 units/g-solid of α-glucosidase and 250 units/g-solid of glucoamylase to hydrolyze remaining soluble starch and by-products, oligosaccharides, and followed by the enzyme treatment at 50° C. for 1 hour. The amount of CMM contained in the treated mixture is determined by HPLC described later in Experiment 1. One unit activity of CMM-forming enzyme is defined as the amount of enzyme which forms one μmole of CMM per minute under the above conditions.

As a concrete example of CMM-forming enzyme, the enzyme having the following physicochemical properties can be used.

(1) Molecular Weight 72,000±20,000 daltons when determined on SDS-PAGE;

(2) Isoelectric Point pI 3.6±0.5 on isoelectrofocusing using ampholine, a carrier ampholyte;

(3) Optimum Temperature 50 to 55° C. when reacted at pH 6.0 for 30 min;

(4) Optimum pH pH 5.5 to 6.0 when reacted at 40° C. for 30 min;

(5) Thermal Stability

Stable up to 30° C. when incubated at pH 6.0 for 60 min

Stable up to 50° C. in the presence of 1 mM $Ca^{2+}$ ion; and (6) pH Stability

Stable in a pH range of 5.0 to 9.0 when incubated at 4° C. for 24 hours;

As an example of CMM-forming enzyme of the present invention, having the above physicochemical properties, may have an amino acid sequence of SEQ ID NO:1 as the N-terminal amino acid sequence.

Usually, CMM-forming enzyme of the present invention has a prescribed amino acid sequence. For example, an amino acid sequence of SEQ ID NO:2 or that homologous to SEQ ID NO:2 ca be listed. A variant enzyme having an amino acid sequence homologous to SEQ ID NO:2 means an enzyme having an amino acid sequence where one or more amino acids in SEQ ID NO:2 are deleted, replaced or added without altering the enzyme activity of acting on α-1,4 glucan having a glucose polymerization degree of 3 or higher and producing CMM. As such a variant enzyme, it is preferable that the enzyme has an amino acid sequence with a homology to SEQ ID NO:2 of, usually, 60% or higher, desirably, 70% or higher, more desirably, 80% or higher, most desirably, 90% or higher.

However, CMM-forming enzyme, having the physicochemical properties or the amino acid sequence described above, is just an example. CMM-forming enzyme of the present invention includes any enzyme having different physicochemical properties or amino acid sequences from the above ones, as long as it produces CMM.

Although CMM-forming enzyme of the present invention is not restricted by its source, bacteria, particularly, the bacterial strain M6 isolated from a soil by the present inventors can be preferably used as the source. The following are the identification results of the strain M6 capable of producing CMM-forming enzyme. The identification of the strain M6 was carried out according to the method as described in "*BISEIBUTSU-NO-BUNRUI-TO-DOTEI*" (Classification and Identification of Microorganisms), edited by Takeji Hasegawa, published by Japan Scientific Societies Press, Tokyo, Japan (1985).

<A. Morphology>

(1) Characteristic of cells when incubated at 27° C. in nutrient agar;
  Existing usually in a rod or coccus shape of 0.4×1.0 to 0.8×3.0 □m,
  Exhibiting polymorphism,
  Possessing motility and asporogenicity, and
  Gram stain, positive;

(2) Characteristic of cells when incubated at 27° C. in EYG agar;
  Exhibiting a rod-coccus cycle.

<B. Cultural Property>

(1) Characteristics of colony formed when incubated at 27° C. in nutrient agar plate;
  Shape: Circular colony having a diameter of 1-2 mm after 3 days incubation
  Rim: Entire
  Projection: Hemispherical shape
  Gloss: Dull
  Surface: Smooth
  Color: Opaque and pale yellow (2) Characteristics of colony formed when incubated at 27° C. in nutrient agar slant;
  Growth: Medium
  Shape: Thread-like (3) Characteristics of colony formed when stub cultured at 27° C. in bouillon and gelatin;
  Not liquefying bouillon and gelatin.

<C. Physiological Properties>

(1) VP-test: Negative
(2) Indole formation: Negative
(3) Hydrolysis of starch: Positive
(5) Formation of pigment: Forming no soluble pigment
(6) Urease: Negative
(7) Oxidase: Positive
(8) Catalase: Positive
(9) Growth conditions: Growing at a pH of 5.5-10.0 and a temperature of 15-37° C.
(10) Oxygen requirements: Aerobic
(11) Major diamino acid of cell wall: Lysine
(12) Peptideglycan type of cell wall: Lysine-Alanine
(13) N-Acyl type of cell wall: Acetyl
(14) Component sugar of cell wall: Galactose, Glucose and Rhamnose
(15) Vitamin requirement: Negative
(16) Mol % of guanine (G) plus cytosine (C) of DNA: 70%, and
(17) DNA-DNA homology: Having a DNA-DNA homology of 69.3% between *Arthrobacter globiformis* ATCC8010

The bacteriological properties were compared with those of known microorganisms with reference to Bergey's Manual of Systematic Bacteriology, Vol. 2 (1986). As a result, it was revealed that the microorganism was identified as of *Artherobacter globiformis*. Based on these results, the present inventors named this microorganism "*Arthrobacter globiformis* M6" and deposited it on Aug. 6, 2003, in International Patent Organism, National Institute of Advanced Industrial Science and Technology, AIST Tsukuba Central 6, 1-1, Higashi 1-Chome Tsukuba-shi, Ibaraki-ken, Japan, and accepted under the accession number of FERM BP-8448.

In addition to the above-mentioned microorganism and its mutant, a microorganism capable of producing CMM-forming enzyme of the present invention includes other microorganisms such as recombinant microorganisms and their mutants, capable of producing CMM-forming enzyme.

The term "the DNA of the present invention" means any DNA encoding the above-mentioned CMM-forming enzyme. The DNA of the present invention includes a DNA originated from the nature and that synthesized artificially as far as the DNA encodes CMM-forming enzyme. Microorganisms of the genus *Arthrobacter*, including *Arthrobacter globiformis* M6 (FERMBP-8448) can be used as the natural sources of the enzyme. A genomic DNA containing the DNA of the present invention can be obtained from the cells of these microorganisms. Specifically, a genomic DNA containing the DNA can be released extracellularly by the steps of inoculating any of the microorganisms into a nutrient medium, culturing about one to three days under aerobic conditions, collecting the cells from the culture, treating the cells with cell-lytic enzymes such as lysozyme and β-glucanase or with ultrasonication. In addition to the methods described above, use of protein-hydrolyzing enzymes such as proteinases, detergents such as SDS and freeze-thaw method are also applicable. The objective DNA can be obtained from the treated cells by using conventional methods in the art, for example, such as phenol-extraction, alcohol-precipitation, centrifugation and ribonuclease-treatment. To artificially synthesize the DNA of the present invention, it can be chemically synthesized based on the amino acid sequence of SEQ ID NO:2. PCR-Method is also applicable to obtain the DNA by using a genomic DNA containing the DNA as a template and an appropriate chemically synthetic DNA as a primer.

The DNA of the present invention has, usually, a prescribed nucleotide sequence, for example, a nucleotide sequence of SEQ ID NO:3 or a nucleotide sequence homologous to SEQ ID NO:3. A variant DNA, having a homologous nucleotide sequence to SEQ ID NO:3, means that having a nucleotide sequence where one or more nucleotides of SEQ ID NO:3 are deleted, replaced or added without altering the activity of the enzyme encoded thereby. The homology of nucleotide sequence to SEQ ID NO:3 of such a variant DNA is preferable to be, usually, 60% or higher, desirably, 70% or higher, more desirably, 80% or higher, most desirably, 90% or higher. The DNA of the present invention encompasses a DNA having a nucleotide sequence where one or more nucleotides of SEQ ID NO:3 are replaced with other nucleotides without altering the encoded amino acid sequence based on the degeneracy of genetic code.

The DNA of the present invention can be advantageously used for constructing a recombinant DNA by inserting to an appropriate self-replicable vector. Recombinant DNAs are usually constructed by a DNA and a self-replicable vector, and they can be relatively easily prepared by conventional recombinant DNA techniques if the DNA is obtained. Such vectors include, for example, plasmid vectors such as pBR322, pUC18, Bluescript II SK(+), pUB110, pTZ4, pC194, pHV14, TRp7, YEp7 and pBS7; and phage vectors such as λgt·λC, λgt·B, ρ11, ϕ1 and ϕ105. To express the DNA of the present invention in *E. coli*, pBR322, pUC18, Bluescript II SK(+), λgt·λC and λgt·λB can be preferably used. While, to express the DNA of the present invention in *Bacillus subtilis*, pUB110, pTZ4, pC194, ρ11, ϕ1 and ϕ105 can be preferably used. Plasmids, pHV14, TRp7, YEp7 and pBS7 are useful in the case of replicating the recombinant DNA in two or more kinds of hosts. In order to insert a DNA into these vectors, conventional methods in the art can be used. Specifically, a DNA is inserted into a vector by the steps of cleaving a genomic DNA containing the objective DNA and a self-replicable vector by restriction enzyme and/or ultrasonication, and ligating the resulting DNA fragment and the resulting vector fragment. The ligation of the DNA fragment and the vector fragment is easily carried out by using a type II-restriction enzymes, particularly, such as Sau 3AI, Eco RI, Hin dIII, Bam HI, Sal I, Xba I, Sac I and Pst I. The desired recombinant DNA is obtainable by ligating them in vivo or in vitro using a DNA ligase, optionally, after annealing the both fragments. The recombinant DNA thus obtained is unlimitedly replicable by the steps of introducing into an appropriate host and culturing the resulting transformant.

The recombinant DNA thus obtained can be introduced into an appropriate host-microorganism such as *E. coli, B. subtilis, Actinomyces* and yeasts. The desired transformant can be obtained by applying the colony-hybridization method or by selecting a transformant by the steps of culturing a transformant in nutrient media containing α-1,4 glucan having a glucose polymerization degree of 3 or higher, and selecting a clone which produces CMM from saccharides.

Any nutrient culture medium can be used for cultivating a microorganism, including a transformant, capable of producing CMM-forming enzyme of the present invention as long as these microorganisms can grow therein and produce CMM-forming enzyme: For example, synthetic- and natural-culture media can be used as nutrient culture media. Any carbon source can be used as long as it is utilized by the microorganisms: Examples of such carbon source are saccharides such as starch and phytoglycogen, obtainable from plants; glycogen and pullulan, obtainable from animals and microorganisms; those hydrolyzates, glucose, fructose, lactose, sucrose, mannitol, sorbitol, and saccharide syrups; and organic acids such as citric acid and succinic acid. The concentrations of these carbon sources in nutrient culture media are appropriately chosen. The nitrogen sources usable in the present invention are, for example, inorganic nitrogen compounds such as ammonium salts and nitrates; organic nitrogen compounds such as urea, corn steep liquor, casein, peptone, yeast extract and beef extract. The inorganic ingredients usable in the invention are, for example, calcium salts, magnesium salts, potassium salts, sodium salts, phosphates, manganese salts, zinc salts, iron salts, copper salts, molybdenium salts, and cobalt salts. If necessary, amino acids and vitamins can be suitably used.

The microorganisms of the present invention are cultured under aerobic conditions, usually, at a temperature in the range of 15-37° C. and at a pH in the range of 5.5-10, preferably, at a temperature in the range of 20-34° C. and at a pH in the range of 5.5-8.5. The cultivation time is set to a time longer than that required for the growth of the microorganisms, preferably, 10-150 hours. The concentration of dissolved oxygen is not specifically restricted, but usually 0.5-20 ppm. The concentration of dissolved oxygen can be kept within the above range by controlling aeration and agitation. The cultivation can be carried out batch-wise or in a continuous manner.

After culturing the microorganisms capable of producing CMM-forming enzyme according to the method described above, the culture containing the enzyme of the present invention is recovered. In the case of culturing a microorganism, *Arthrobacter globiformis* M6 (FERM BP-8448), the major activity of CMM-forming enzyme is found in the cell-free supernatant. Both the cell-free supernatant and the culture can be used as a crude enzyme. Conventional liquid-solid separation methods can be employed to remove cells from the culture. For example, methods to directly centrifuge the resultant culture, as well as those to filtrate the culture with pre-coated filters or to separate cells by membrane filtration using plane filter or follow fibers, can be suitably used. While cell-free supernatants thus obtained can be used intact as a crude enzyme solution, they may be concentrated prior to use. The concentration methods usable in the invention are, for example, salting out using ammonium sulfate, sedimentation using acetone or alcohol, and concentration using membranes such as plane filters and follow fibers.

CMM-forming enzyme can be subjected to conventional immobilization using cell-free supernatants and their concentrates. Examples for such conventional methods are conjugation methods using ion exchangers, covalent bindings and adsorptions using resins and membranes, and inclusion methods using high molecular weight substances.

As described above, a crude enzyme solution can be used intact after concentrating it as CMM-forming enzyme of the present invention. Further, CMM-forming enzyme can be advantageously used after separating or purifying the crude enzyme solution by suitable conventional methods used in the art. For example, a purified CMM-forming enzyme preparation exhibiting an electrophoretically single band can be obtained by dialyzing a crude enzyme preparation which had been salting out a cell-free supernatant or disrupted cells with ammonium sulfate and concentrating the resultant; and successively purifying the dialyzed solution on anion-exchange column chromatography using "DEAE-TOYOPEARL 650S"; hydrophobic chromatography using "PHENYL-TOYOPEARL 65CM".

In the case of producing CMM-forming enzyme as a recombinant enzyme, the enzyme may be accumulated intracellularly, depending on the kinds of host microorganisms. In such cases, while the cell or the culture can be used intact, the recombinant enzyme can be advantageously used after extracting it from cells by using osmotic-shock methods or detergents or by disrupting cells using ultrasonication methods or cell-wall digesting enzymes; and separating it from cell or cell debris.

CMM-forming enzyme of the present invention, thus obtained, acts on α-1,4 glucan having a glucose polymerization degree of 3 or higher and produces CMM having a structure of cyclo{>6)-α-D-glucopyranosyl-(1>4)-α-glucopyranosyl-(1>6)-α-glucopyranosyl-(1>4)-α-glucopyranosyl-(1>}. It was revealed that the enzyme produces CMM having a structure of cyclo{>6)-α-D-lucopyranosyl-1>4)-α-glucopyranosyl-(1>6)-α-g lucopyranosyl-(1>4)-α-glucopyranosyl-(1>} by the steps of acting on α-1,4 glucan having a glucose polymerization degree of 3 or higher, transferring □-maltosyl moiety by the intermolecular transglycosylation to form 6-□-maltosyl 0-1,4 glucan where α-maltosyl moiety is bound to hydroxyl group at C-6 position at the non-reducing end glucose of α-1,4 glucan, and cyclizing the 6-α-maltosyl α-1,4 glucan to form CMM having a structure of cyclo{>6)-α-D-glucopyranosyl-(1>4)-α-glucopyranosyl-(1>6)-α-glucopyranosyl-(1>4)-α-glucopyranosyl-(1>}. Particularly, CMM-forming enzyme of the present invention may have the following physicochemical properties:

(1) Molecular Weight 72,000±20,000 daltons when determined on SDS-PAGE;

(2) Isoelectric Point pI 3.6±0.5 on isoelectrofocusing ampholine, a carrier ampholyte;

(3) Optimum Temperature 50 to 55° C. when reacted at pH 6.0 for 30 min;

(4) Optimum pH pH 5.5 to 6.0 when reacted at 40° C. for 30 min;

(5) Thermal Stability

Stable up to 30° C. when incubated at pH 6.0 for 60 min

Stable up to 50° C. in the presence of 1 mM $Ca^{2+}$ ion;

(6) pH Stability

Stable in a pH range at 5.0 to 9.0 when incubated at 4° C. for 24 hours; and (7) N-Terminal Amino Acid Sequence Having an amino acid sequence of SEQ ID NO:1, i.e. Asp-Pro-Thr-Thr-Ser α-1,4 Glucan having a glucose polymerization degree of 3 or higher, which can be used as a substrate of CMM-forming enzyme of the present invention, includes starch, amylose, amylopectin, glycogen, and their partial hydrolyzates such as amylodextrins, maltodextrins, maltooligosaccharides, obtainable by partially hydrolyzing them with amylases and acids. The partial hydrolyzates obtainable by hydrolyzing starch, amylose, amylopectin, and glycogen by using amylase such as α-amylase (EC 3.2.1.1), maltotetraose-forming amylase (EC 3.2.1.60), and maltohexaose-forming amylase (EC 3.2.1.98), described in "Handbook of Amylases and Related Enzymes" published by Pergamon Press Inc., (Tokyo), 1988, can be used as the partial hydrolyzates prepared by hydrolyzing with amylases. Further, starch-debranching enzymes such as pullulanase (EC 3.2.1 41) and isoamylase (EC 3.2.1.68) can be arbitrarily used for preparing the partial hydrolyzates.

Both subcelestal starches such as those from corn, wheat, rice, etc., and subterranean starches such as those from potato, sweet potato, tapioca, etc., can be used as substrates. The substrate can be preferably used in the form of a solution prepared by gelatinizing and/or liquefying starch. The CMM content in the reaction mixture is increased with decrease of the degree of partial hydrolysis of starch. Therefore, it is preferable that the DE of the partial starch hydrolyzate is, usually, about 20 or lower, desirably, about 12 or lower, more desirably, about 5 or lower. The CMM content as referred to as in the present specification means the value which is calculated by the following formula:

$$\text{CMM content (\%)}=\{(\text{Weight of CMM formed})/(\text{Total weight of saccharides in the reaction mixture})\}\times 100$$

When CMM-forming enzyme is allowed to act on a substrate, the substrate concentration is not specifically restricted. For example, the reaction by CMM-forming enzyme of the present invention proceeds to form CMM even in the case of using a substrate solution with a relatively low concentration such as 0.1% (w/v). For industrial production, the substrate concentration is preferable to be 1% (w/v) or higher, and CMM can be advantageously produced under the condition. Also, suspensions with a high concentration, containing insoluble substrates can be used as the substrate solutions. The reaction temperature used in the present enzymatic reaction can be set to a temperature at which the reaction proceeds, i.e. a temperature up to about 60° C., preferably, a temperature in a range of 30 to 50° C. The reaction pH is controlled in the range of, usually, 5 to 9, preferably, 5 to 7. Since the amount of enzyme and reaction time are closely related, the conditions are adequately chosen with respect to the progress of the objective enzymatic reaction.

CMM of the present invention can be obtained in a high content, about 30% or higher from starch or its partial hydrolyzate, about 44% from amylose, by allowing CMM-forming enzyme of the present invention to act on, for example, 1% (w/v) substrate solution containing starch, its partial hydrolyzate, or amylose. The mechanism of CMM-formation by CMM-forming enzyme is estimated as follows:

(1) The enzyme acts on α-1,4 glucan having a glucose polymerization degree of 3 or higher as the substrates and forms 6-α-maltosyl-α-1,4 glucan whose glucose polymerization degree is increased by two, having 6-α-maltosyl moiety at the non-reducing end, and α-1,4 glucan whose glucose polymerization degree is decreased by two by catalyzing an intermolecular 6-α-maltosyl transferring reaction to transfer a maltosyl moiety at the non-reducing end of the substrate to hydroxyl group at the C-6 position of the non-reducing end glucose of another α-1,4 glucan molecule.

(2) The enzyme further acts on 6-α-maltosyl-α-1,4 glucan and forms CMM having a structure of cyclo{>6)-α-D-glucopyranosyl-(1>4)-α-D-glucopyranosyl-(1>6)-α-D-glucopyranosyl-(1>4)-α-D-glucopyranosyl-(1>} and maltooligosaccharide whose glucose polymerization degree is decreased by four, by catalyzing an intramolecular α-maltosyl-transferring reaction to cyclize and to form CMM.

(3) CMM is formed from α-1,4 glucan newly formed in the above 1) and 2), by the reaction described in the above 1) and 2).

In the above CMM-forming reaction, CMM content in the reaction mixture can be advantageously improved by using other enzymes together with CMM-forming enzyme. For example, CMM content in the reaction mixture can be advantageously improved by allowing CMM-forming enzyme together with starch-debranching enzymes such as isoamylase to act on starch.

The reaction mixture, thus obtained by the above reaction, can be used intact as a saccharide solution comprising CMM. Optionally, the saccharide solution comprising CMM can be used after hydrolyzing concomitant oligosaccharides by allowing one or more enzymes selected from the group consisting of α-amylase, β-amylase, glucoamylase, and α-glucosidase to act on the solution. Usually, a saccharide solution comprising CMM is used after purification. Conventional methods used for purifying saccharides can be arbitrarily selected as the purification method. For example, one or more purification methods selected from the group consisting of decoloring with an activated charcoal; desalting with ion exchange resins in H- and OH-form; fractionation by column chromatography such as ion exchange column chromatography, charcoal column chromatography, and silica gel column chromatography; separation using organic solvents such as alcohol and acetone; separation using a membrane having a suitable separability; fermentation using microorganisms, which utilize and decompose concomitant saccharides but does not utilize CMM, such as yeasts; and eliminating the remaining reducing sugar with alkaline treatments; can be arbitrarily used.

More particularly, ion exchange column chromatography can be suitably used as an industrial-scale preparation of the objective saccharides. The objective CMM or a saccharide composition comprising the same with an improved purity can be advantageously prepared by, for example, column chromatography using a strongly acidic cation exchange resin as described in Japanese Patent Kokai Nos. 23,799/83 and 72,598/83 to remove concomitant saccharides. In this case, any one of fixed bed, moving bed, and semi-moving bed methods can be employed.

A solution comprising CMM, thus obtained, or a saccharide solution with an improved purity of CMM contains CMM in an amount of, usually, 10% (w/w) or higher, desirably, 40% (w/w) or higher, on a dry solid basis, and is usually concentrated to make into a product in a syrupy form. The syrupy product can be arbitrarily dried to make into a powdery product.

In order to prepare crystalline CMM, an about 5 to 90% (w/w) solution comprising CMM with a purity of about 50% or higher is placed in a crystallizer, and gradually cooled while stirring in the presence of 0.1 to 20% (w/w) seed crystal at a temperature of 95° C. or lower, preferably, 10 to 90° C., to obtain a massecuite containing crystalline CMM. Centrifugation can be employed to produce crystalline CMM from the massecuite. Conventional methods such as block pulverization, fluidized-bed granulation, and spray-drying can be employed to prepare crystalline saccharides containing the mother liquor from the massecuite. The resulting crystalline CMM or crystalline saccharides containing the mother liquor obtained according to the present invention is a non-reducing white powder with a mild and relatively low sweetness and relatively higher stability. Because of this, these saccharides can be mixed and processed with other materials, especially, amino acids and amino acid-containing substances such as oligopeptides and proteins without fear of causing browning, smell and deterioration of other materials.

Further, CMM of the present invention has clathrating ability and prevents the volatilization and deterioration of clathrated flavors and effective ingredients. Therefore, CMM can be used for stabilizing and keeping flavors and effective ingredients. In this case, the stabilizing effect by clathrating using CMM can be advantageously enhanced by using CMM together with other cyclic saccharides such as cyclodectrins, branched cyclodextrins, a cyclic tetrasaccharide having a structure of cyclo{>6)-α-D-glucopyranosyl-(1>3)-α-D-lucopyranosyl-1>6)-α-D-glucopyranosyl-(1>3)-α-D-g lucopyranosyl-(1>} which is disclosed in International Patent Publication Nos. WO 01/90338 A1, WO 02/055708 A1, and WO 02/40659 A1 by the same applicant as the present invention, branched cyclic tetrasaccharides, cyclodextrans, cyclofructans, etc. The cyclic saccharides such as cyclodextrins are not restricted to products with high purities. For example, a starch hydrolyzate comprising various cyclic saccharides together with a large amount of maltodextrins can be advantageously used as cyclic saccharides with low purities.

In addition, CMM of the present invention is not substantially hydrolyzed by amylase and α-glucosidase. Therefore, CMM is not digested and adsorbed when orally taken, and is hardly fermented by intestinal bacteria. Since CMM has a remarkably low calorie, it can be used as a substance like a water-soluble dietary fiber. In the case of using CMM of the present invention as a powdery product, it shows a relatively low hygroscopicity and has a low adhesiveness and solidification. The product can be used for preventing adhesion and solidification of powdery products produced by mixing it with other powders. Intact CMM is a novel sweetener with no toxicity and no harm.

A crystalline CMM can be advantageously used for tablets and sugar-coated tablets in combination with binders such as pullulan, hydroxyethyl starch, and polyvinylpyrrolidone because CMM per se is a stable sweetener. Furthermore, CMM of the present invention has properties of osmosis-controlling ability, filler-imparting ability, gloss-imparting ability, moisture-retaining ability, viscosity, crystallization-preventing ability for other sugars, less-fermentable property, etc.

Thus, CMM and the saccharide compositions comprising the same of the present invention can be advantageously used as a sweetener, taste-improving agent, quality-improving agent, stabilizer, color-deterioration preventing agent, excipient, etc., for various compositions such as foods and beverages, favorite products, feeds, baits, cosmetics, pharmaceuticals, etc.

CMM of the present invention and the saccharide compositions comprising the same can be used intact as a seasoning for sweetening products. If necessary, they can be advantageously used in combination with other sweeteners, for example, powdery syrup, glucose, isomerized sugar, sucrose, maltose, trehalose, honey, maple sugar, sorbitol, maltitol, dihydrochalcone, stevioside, α-glycosyl stevioside, sweetener of *Momordica grosvenori*, glycyrrhizin, thaumatin, sucralose, L-aspartyl L-phenylalanine methyl ester, saccharine, glycine and alanine; and fillers such as dextrin, starch, and lactose.

Further, powdery products of CMM of the present invention and the saccharide compositions comprising the same can be arbitrarily used intact or, if necessary, after mixing with fillers, excipients, binders, etc., and then shaped into various shapes such as granules, spheres, sticks, plates, cubes, and tablets.

CMM of the present invention and the saccharide compositions comprising the same have sweetness which well harmonize with other materials having sour-, salty-, astringent-, delicious-, and bitter-taste; and have a high acid- and heat-tolerance. Thus, they can be advantageously used to sweeten and/or improve the taste and quality of general food products.

CMM of the present invention and the saccharide compositions comprising the same can be advantageously used as a sweetener, taste-improving agent, and quality-improving agent for various seasonings such as a soy sauce, powdered soy sauce, miso, "funmatsu-miso" (a powdered miso), "moromi" (a refined sake), "hishio" (a refined soy sauce), "furikake" (a seasoned fishmeal), mayonnaise, dressing, vinegar, "sanbai-zu" (a sauce of sugar, soy sauce and vinegar), "funmatsu-sushi-zu" (powdered vinegar for sushi), "chuka-no-moto" (an instant mix for Chinese dish), "tentsuyu" (a sauce for Japanese deep fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar, and coffee sugar. Also, CMM and the saccharide compositions comprising the same can be advantageously used to sweeten and to improve the taste and quality of various "wagashi" (Japanese cakes) such as "senbei" (a rice cracker), "arare" (a rice cake cube), "okoshi" (a millet and rice cake), "gyuhi" (a starch paste), "mochi" (a rise paste) and the like, "manju" (a bun with a bean-jam), "uiro" (a sweet rice jelly), "an" (a bean-jam) and the like, "yokan" (a sweet jelly of beans), "mizu-yokan" (a soft azuki-bean jelly), "kingyoku" (a kind of yokan), jelly, pao de Castella, and "amedama" (a Japanese toffee); Western confectioneries such as a bun, biscuit, cracker, cookie, pie, pudding, butter cream, custard cream, cream puff, waffle, sponge cake, doughnut, chocolate, chewing gum, caramel, nougat, and candy; frozen desserts such as an ice cream and sherbet; syrups such as a "kajitsu-no-syrup-zuke" (a preserved fruit)

and "korimitsu" (a sugar syrup for shaved ice); pastes such as a flour paste, peanut paste, and fruit paste; processed fruits and vegetables such as a jam, marmalade, "syrup-zuke" (fruit pickles), and "toka" (conserves); pickles and pickled products such as a "fukujin-zuke" (red colored radish pickles), "bettara-zuke" (a kind of whole fresh radish pickles), "senmai-zuke" (a kind of sliced fresh radish pickles), and "rakkyo-zuke" (pickled shallots); premix for pickles and pickled products such as a "takuan-zuke-no-moto" (a premix for pickled radish), and "hakusai-zuke-no-moto" (a premix for fresh white rape pickles) meat products such as a ham and sausage; products of fish meat such as a fish ham, fish sausage, "kamaboko" (a steamed fish paste), "chikuwa" (a kind of fish paste), and "tenpura" (a Japanese deep-fat fried fish paste); "chinmi" (relish) such as a "uni-no-shiokara" (salted guts of urchin), "ika-no-shiokara" (salted guts of squid), "su-konbu" (processed tangle), "saki-surume" (dried squid strips), "fugu-no-mirin-boshi" (a dried mirin-seasoned swell-fish), seasoned fish flour such as of Pacific cod, sea bream, shrimp, etc.; "tsukudani" (foods boiled down in soy sauce) such as those of layer, edible wild plants, dried squid, small fish, and shellfish; daily dishes such as a "nimame" (cooked beans), potato salad, and "konbu-maki" (a tangle roll); milk products; canned and bottled products such as those of meat, fish meat, fruit, and vegetable; alcoholic beverages such as a synthetic sake, fermented liquor, sake, fruit liquor, low-malt beer and beer; soft drinks such as a coffee, cocoa, juice, carbonated beverage, sour milk beverage, and beverage containing a lactic acid bacterium; instant food products such as instant pudding mix, instant hot cake mix, instant juice, instant coffee, "sokuseki-shiruko" (an instant mix of azuki-bean soup with rice cake), and instant soup mix; and other foods and beverages such as solid foods for babies, foods for therapy, drinks, peptide foods, and frozen foods.

CMM and the saccharide compositions comprising the same can be arbitrarily used to improve the taste preference of feeds and pet foods for animals and pets such as domestic animals, poultry, honey bees, silk warms, and fishes; and also they can be advantageously used as a sweetener and taste-improving agent, taste-curing agent, quality-improving agent, and stabilizer for various compositions including favorite products, cosmetics, and pharmaceuticals in a paste or liquid form such as tobacco, cigarette, toothpaste, lipstick, rouge, lip cream, internal liquid medicine, tablet, troche, cod-liver oil in the form of drop, oral refrigerant, cachou, and gargle.

When used as a quality-improving agent or stabilizer, CMM and the saccharide compositions comprising the same can be advantageously used in biologically active substances susceptible to lose their effective ingredients and activities, as well as in health foods, functional foods, and pharmaceuticals containing the biologically active substances. Example of such biologically active substances are liquid preparations containing lymphokines such as α-, β-, and γ-interferons, tumor necrosis factor-α (TNF-α), tumor necrosis factor-β (TNF-β), macropharge migration inhibitory factor, colony-stimulating factor, transfer factor, and interleukin 2; liquid preparations containing hormones such as insulin, growth hormone, prolactin, erythropoietin, and follicle-stimulating hormone; liquid biological preparations such as BCG vaccine, Japanese encephalitis vaccine, measles vaccine, live polio vaccine, small pox vaccine, tetanus toxoid, Trimeresurus antitoxin, and human immunoglobulin; liquid preparations containing antibiotics such as penicillin, erythromycin, chloramphenicol, tetracycline, streptomycin, and kanamycin sulfate; liquid preparations containing vitamins such as thiamin, riboflavin, L-ascorbic acid, cod liver oil, carotenoid, ergosterol, tocopherol; highly unsaturated fatty acids and their derivatives such as EPA, DHA and arachidonic acid; solution of enzymes such as lipase, esterase, urokinase, protease, β-amylase, isoamylase, glucanase, and lactase; extracts such as ginseng extract, turtle extract, *chlorella* extract, aloe extract and propolis extract; biologically active substances such as living microorganisms paste of virus, lactic acid bacteria, and yeast, and royal jelly. By using CMM and the saccharide compositions comprising the same, the above biologically active substances can be arbitrary prepared in health foods, functional foods, and pharmaceuticals in a liquid, paste, or solid form, which have a satisfactorily-high stability and quality with less fear of losing or inactivating their effective ingredients and activities.

The methods for incorporating CMM or the saccharide composition comprising the same into the aforesaid compositions are those which can incorporate CMM and the saccharide compositions into the compositions before completion of their processing, and which can be appropriately selected from the following conventional methods; mixing, kneading, dissolving, melting, soaking, penetrating, dispersing, applying, coating, spraying, injecting, crystallizing, and solidifying. The amount of CMM or the saccharide compositions comprising the same to be preferably incorporated into the final compositions is usually in an amount of 0.1% or higher, desirably, 1% or higher.

The following experiments explain the present invention in detail.

Experiment 1

Preparation of a Non-reducing Saccharide

A liquid culture medium consisting of 1.5% (w/v) of "PINE-DEX #4", a partial starch hydrolyzate commercialized by Matsutani Chemical Industries Co., Ltd., Hyogo, Japan, 0.5% (w/v) of "POLYPEPTONE", a yeast extract commercialized by Nihon Pharmaceutical Co., Ltd., Tokyo, Japan, 0.1% (w/v) of "YEAST EXTRACT S", a yeast extract commercialized by Nihon Pharmaceutical Co., Ltd., Tokyo, Japan, 0.1% (w/v) of dipotassium phosphate, 0.06% (w/v) of sodium phosphate dodeca-hydrate, 0.05% (w/v) of magnesium sulfate hepta-hydrate, 0.3% (w/v) of calcium carbonate, and water was placed in twelve 500 ml-Erlenmeyer flasks in a respective amount of 100 ml, sterilized by autoclaving at 121° C. for 20 min, and Nov. 16, 2007 cooled. Successively, the culture medium was inoculated with *Arthrobacter globiformis* M6, FERM BP-8448, and followed the cultivation under rotary-shaking conditions at 27° C. and 230 rpm for 120 hours. After completion of the culture, about 1.1 L of the culture supernatant was obtained by centrifuging the culture broth to remove cells. One liter of the resulting culture supernatant was used as an enzyme preparation and admixed with one liter of 50 mM acetate buffer containing 2% (w/v) of soluble starch and 2 mM of calcium chloride and followed by the reaction at 40° C. for 24 hours. The reaction was stopped by heating at about 100° C. for 10 min.

To examine the saccharides in the resulting reaction mixture, saccharides were separated by silica gel thin-layer chromatography (hereinafter, simply abbreviated as "TLC") using "KIESELGEL 60", a TLC aluminum plate (10×20 cm) and a solvent (n-butanol/pyridine/water, volume ratio of 6:4:1) and two-times ascending method. The separated saccharide on the plate were detected by visualizing the spots with sulfate-methanol method, and glucose with a Rg value of 1.00, maltose with a Rg value of 0.82, and two kinds of unknown saccharides with Rg values of about 0.44 and about 0.21 were detected. It was considered that the two kinds of unknown saccharides were formed from soluble starch by the action of an enzyme in the culture supernatant obtained from *Arthrobacter globiformis* M6. The above "Rg value" means a rate of solute migration distance to glucose migration distance on TLC and it is calculated by the following equation:

*Rg* value=(solute migration distance/glucose migration distance)

Successively, the above reaction mixture was adjusted to pH 5.0 using hydrochloric acid, then admixed with 4,000 units/g-dry solid of "TRANSGLUCOSIDASE-LAMANO", α-glucosidase commercialized Amano Enzyme Inc., Aichi, Japan, and 250 units/g-dry solid of glucoamylase commercialized by Nagase ChemteX Corporation, Osaka, Japan, and followed by the reaction at 50° C. for 16 hours. After completion of the reaction, the reaction was stopped by heating at about 100° C. for 10 min. The resulting reaction mixture was subjected to TLC analysis to reveal the saccharides in the mixture. As a result, glucose and the saccharide showing Rg value of about 0.44 were detected but maltose and the saccharide showing Rg value of about 0.21 were not. This result revealed that maltose and the saccharide showing Rg value of about 0.21 are hydrolyzed into glucose by α-glucosidase and glucoamylase but the saccharide showing Rg value of about 0.44 is not.

Successively, the pH of the reaction mixture was adjusted to 12 by adding sodium hydroxide, and the resulting mixture was incubated at 98° C. for one hour to decompose reducing sugars. After removing insoluble substances by filtrating the reaction mixture, the resulting filtrate was decolored and desalted using "DIAION SK-1B", an ion exchange resin commercialized by Mitsubishi Chemical Corporation, Tokyo, Japan, and "IRA 411", an anion exchange resin commercialized by Organo Corporation, Tokyo, Japan. The resulting solution was filtrated, concentrated using an evaporator, and dried in vacuo to obtain about 4.0 g of a powdery saccharide, on a dry solid basis.

Figure 1:
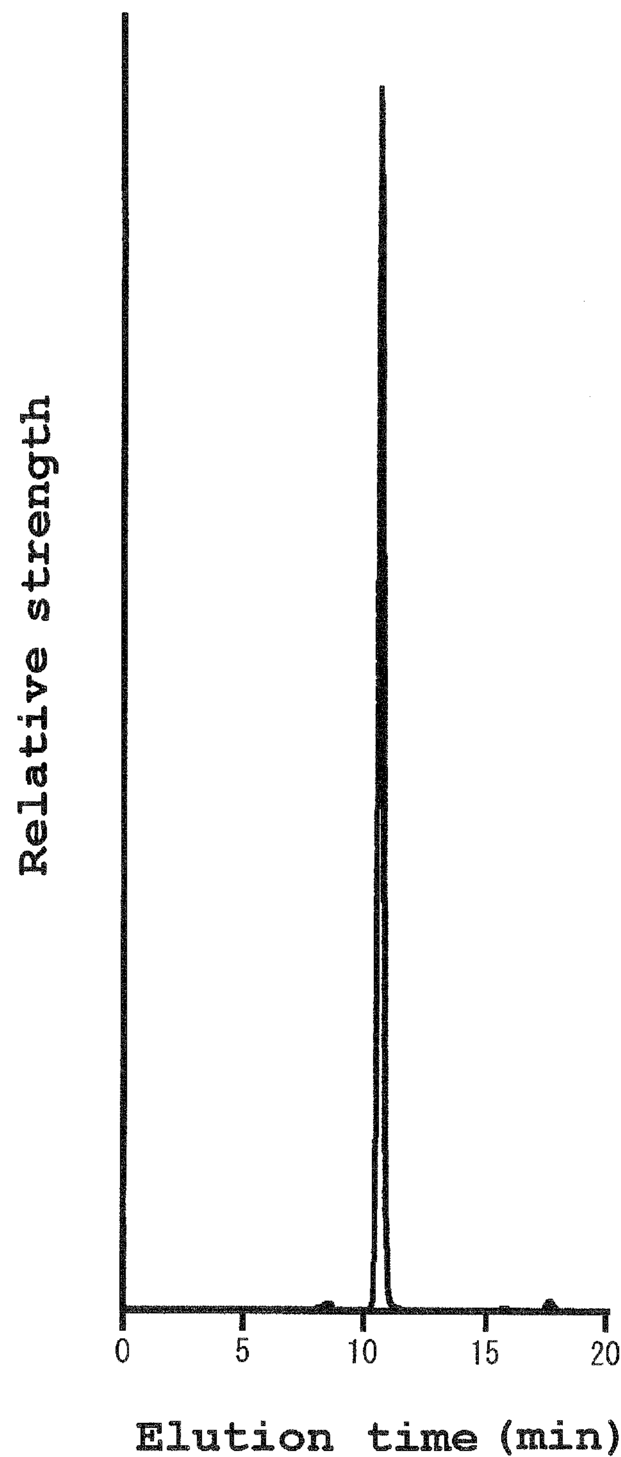
FIG. 1 shows the HPLC elution pattern of the preparation of non-reducing saccharide.

The saccharide, thus obtained, was subjected to high performance liquid chromatography (abbreviated as "HPLC", hereinafter) to analyze the saccharide composition. As shown in FIG. 1, a peak was detected at a retention time of 10.61 min, revealing that the purity of the saccharide is extremely high, i.e., 97% or higher. HPLC was carried out under the following conditions:

Column: "Shodex SUGAR KS-801", produced by Showa Denko K. K., Tokyo, Japan

Eluent: Water

Column temperature: 60° C.

Flow rate: 0.5 ml/min

Detector: "RI-8012", a refractive index detector produced by Tosoh Corporation, Tokyo, Japan.

The reducing power of the saccharide was measured by the Somogyi-Nelson method, revealing that it was less than the measurable limit. It was concluded that the saccharide was a non-reducing saccharide substantially.

Experiment 2

Structural Analyses of the Non-reducing Saccharide

Experiment 2-1

Mass Spectrometry

The mass of the non-reducing saccharide obtained by the method in Experiment 1 was analyzed using "LCQ Advantage", a mass spectrometer commercialized by Theremo Electron K.K., Kanagawa, Japan. A sodium-added molecular ion with a mass of 671 was remarkably detected and the data revealed that the mass of the non-reducing saccharide of the present invention was 648.

Experiment 2-2

Analysis of Component Sugar

According to conventional method, the component sugar of the non-reducing saccharide obtained by the method in Experiment 1 was examined by hydrolyzing the saccharide to monosaccharide with diluted sulfuric acid and analyzing the resulting hydrolyzate by using gas chromatography. Only D-glucose was detected in the hydrolyzate, revealing that the saccharide was constructed with D-glucose. Considering with the above mass, it was revealed that the non-reducing saccharide of the present invention was a cyclic saccharide composed of four D-glucose molecules.

Experiment 2-3

Methylation Analysis

According to conventional method, the non-reducing saccharide obtained by the method in Experiment 1 was subjected to methylation analysis, and the resulting methylated products were analyzed by gas chromatography. The result is in Table 1.

TABLE 1

| Methylation product | Ratio |
|---|---|
| 2,3,4-Trimethylated product | 1.03 |
| 2,3,6-Trimethylated product | 1.00 |

As is evident from the result in Table 1, 2,3,4-trimethylated product and 2,3,6-trimethylated product were detected in equimolar amount. Therefore, it was revealed that the non-reducing saccharide, constructed by four D-glucose molecules, of the present invention was constructed by two D-glucose molecules whose hydroroxyl groups at C-1 and C-6 positions were bound with other D-glucose molecule viaglucosidic linkages and two D-glucose molecules whose hydroxyl groups at C-1 and C-4 positions were bound with other D-glucose molecules via glucosidic linkages.

Experiment 2-4

Nuclear Magnetic Resonance (NMR) Analysis

Figure 2:
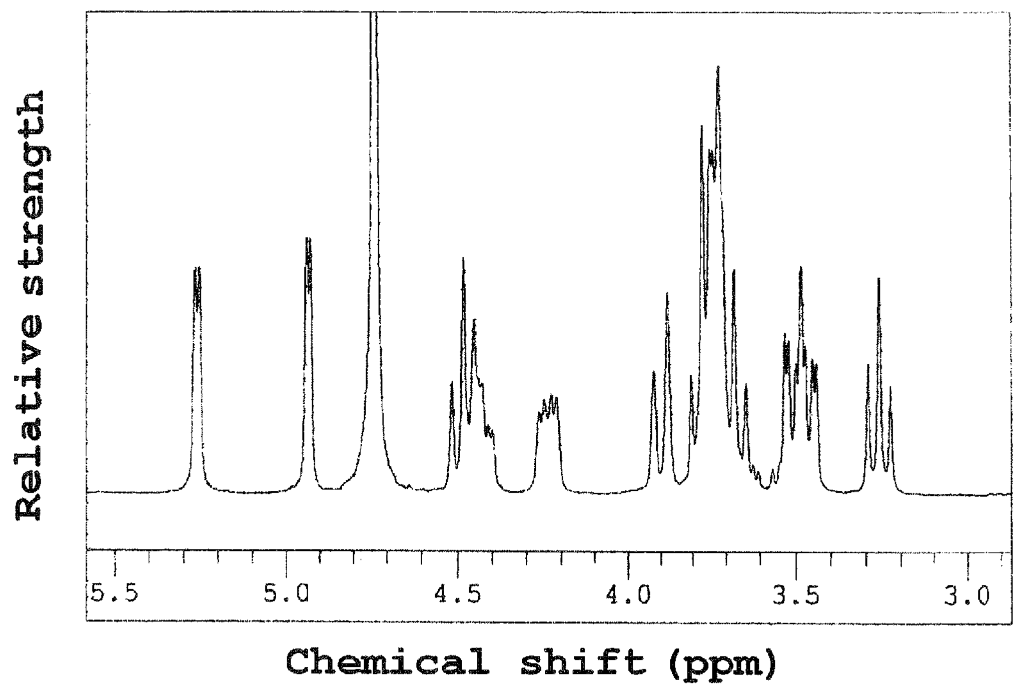
FIG. 2 shows the $^{1}$H-NMR spectrum of the isolated non-reducing saccharide.
Figure 3:
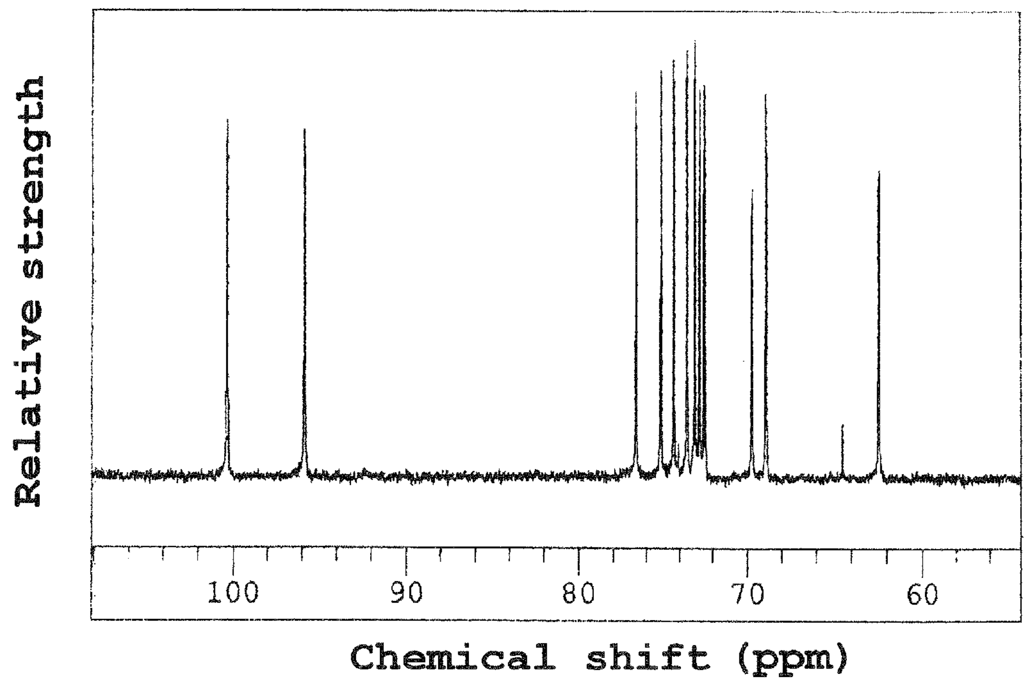
FIG. 3 shows the $^{13}$C-NMR spectrum of the isolated non-reducing saccharide.

According to conventional method, the non-reducing saccharide was subjected to NMR analysis. Its $^{1}$H-NMR spectrum and $^{13}$C-NMR spectrum are in FIGS. 2 and 3, respectively. Although the results in Experiments 2-1 and 2-2 indicated the non-reducing saccharide to be constructed by four glucose molecules, only 12 signals of carbon atom were detected in its $^{13}$C-NMR spectrum. From the result, it was revealed that the non-reducing saccharide was a cyclic tetrasaccharide having a symmetrical structure. Two signals, at about 4.93 ppm and about 5.26 ppm, in $^{1}$H-NMR spectrum were assigned to proton at C-1 position of D-glucose residue, and these spin-spin coupling constants were about 3.309 Hz (signal at about 4.93 ppm) and about 3.677 Hz (signal at about 5.26 ppm), respectively. From the results, it was revealed that both anomer types of hydroxyl groups at C-1 position of D-glucose residue bound via the 1,4-glucosidic and the 1,6-glucosidic linkages were α-type.

Figure 4:
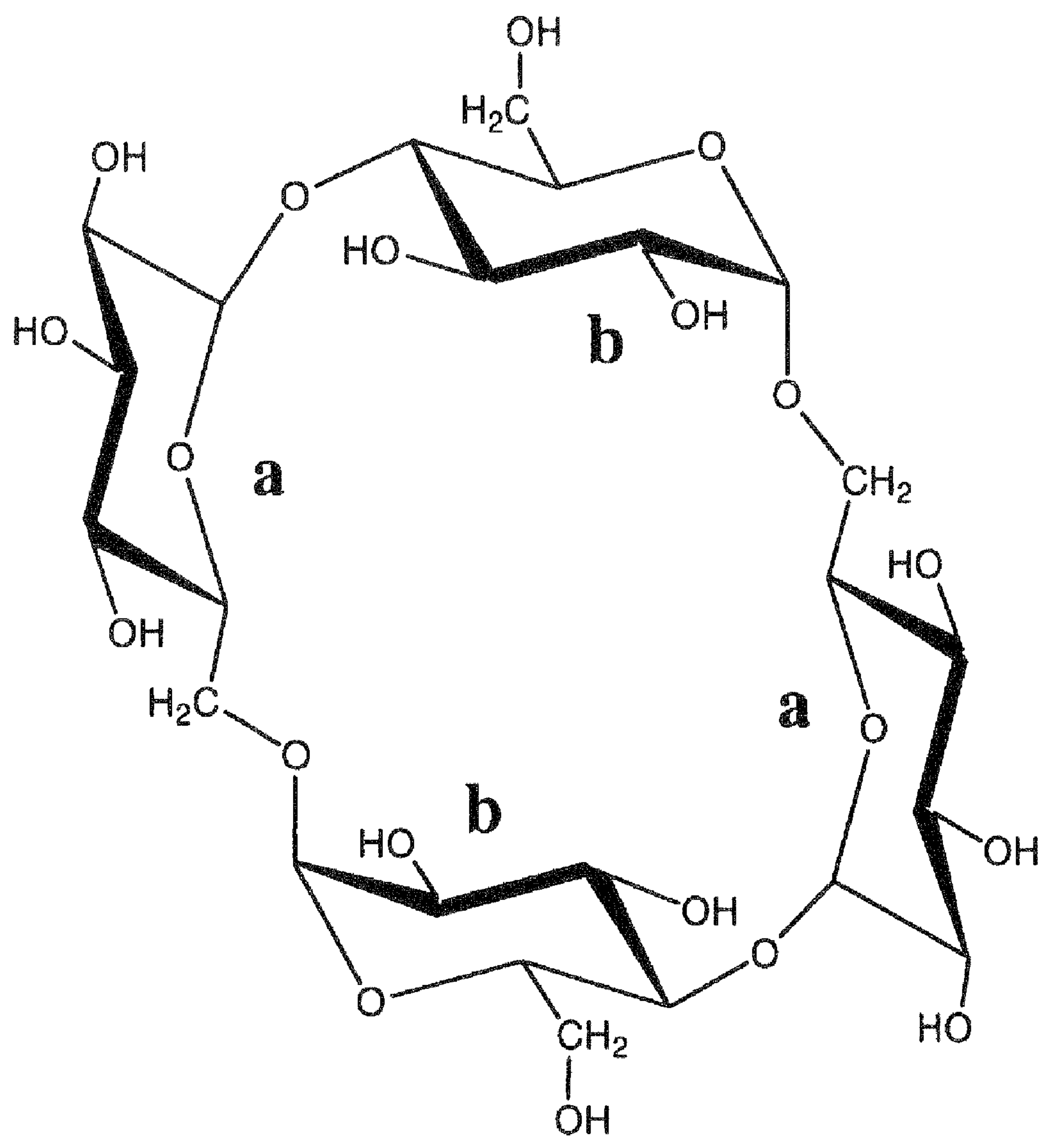
FIG. 4 shows the structure of CMM of the present invention.

From the above results, it was revealed that the non-reducing saccharide of the present invention is cyclic maltosylmaltose shown in FIG. 4, i.e. a cyclic tetrasaccharide having a structure of cyclo{>6)-α-D-glucopyranosyl-(1>4)-α-D-glucopyranosyl-(1>6)-α-D-glucopyranosyl-(1>4)-α-D-glucopyranosyl-(1>}. Since the saccharide, having the above structure, has been unknown before, CMM of the present invention is a novel cyclic saccharide.

Experiment 3

Preparation of CMM-forming Enzyme

The liquid culture medium, described in Experiment 1, was placed in two 500 ml-Erlenmeyer flasks in a respective amount of 100 ml, sterilized by autoclaving at 121° C. for 20 min, cooled and inoculated with *Arthrobacter globiformis* M6, FERM BP-8448, and followed by culturing under rotary-shaking conditions at 27° C. and 230 rpm for 48 hours to prepare a seed culture.

About 20 L of a fresh preparation of the same liquid culture medium as used in the above seed culture were placed in a 30-L fermenter, sterilized by heating, and then cooled to 27° C. and inoculated with about 200 ml of the seed culture, followed by the cultivation at 27° C. and pH 5.5 to 8.0 for 96 hours under aeration-agitation conditions. After completion of the cultivation, the resulting culture broth was distilled from the fermenter and removed cells by centrifuging at 8,000 rpm for 20 min, and about 18 L of culture supernatant was obtained. CMM-forming enzyme activities in the culture broth and culture supernatant were assayed. About 0.028 unit/ml and about 0.026 unit/ml of the enzyme activities were detected in the culture broth and the culture supernatant, respectively. It was revealed that major part of CMM-forming enzyme of the present invention, produced by *Arthrobacter globiformis* M6, was secreted extracellularly.

Experiment 4

Purification of CMM-forming Enzyme

About 9.2 L (Total activity: about 240 units) of the culture supernatant obtained in Experiment 3 was salted out by adding ammonium sulfate to give finally 60% saturation and allowing it to stand at 4° C. for 24 hours. The resultant precipitates were collected by centrifuging at 11,000 rpm for 30 min, dissolved in 10 mM Tris-HCl buffer (pH 7.5), and dialyzed against the same buffer to obtain about 240 ml of a crude enzyme solution. The crude enzyme solution had about 0.83 unit/ml (Total activity: about 200 units) of CMM-forming enzyme. The crude enzyme solution was subjected to anion-exchange column chromatography using 100 ml of "DEAE-TOYOPEARL 650S" gel, an anion-exchange gel commercialized by Tosoh Corporation, Tokyo, Japan. CMM-forming enzyme activity was adsorbed on "DEAE-TOYOPEARL 650S" gel pre-equilibrated with 10 mM Tris-HCl buffer (pH 7.5) and when eluted with a linear gradient increasing from 0 M to 0.4 M of sodium chloride, CMM-forming enzyme activity was eluted at about 0.22 M of sodium chloride. The active fractions were collected and added ammonium sulfate to give a final concentration of 1 M, and then allowed to stand at 4° C. for 24 hours. The enzyme solution was centrifuged to remove precipitates, and subjected to hydrophobic column chromatography using 10 ml of "PHENYL-TOYOPEARL 650M" gel, a gel commercialized by Tosoh Corporation, Tokyo, Japan. CMM-forming enzyme activity was adsorbed on "PHENYL-TOYOPEARL 650M" gel pre-equilibrated with 20 mM acetate buffer (pH 6.0) containing 1 M of ammonium sulfate and when eluted with a linear gradient decreasing from 1 M to 0 M of ammonium sulfate, CMM-forming enzyme activity was eluted at about 0.1 M of ammonium sulfate. The amount of enzyme activity, specific activity and yield of CMM-forming enzyme in each purification step are in Table 2.

TABLE 2

| Purification step | Enzyme* activity (units) | Specific activity of enzyme* (units/mg-protein) | Yield (%) |
|---|---|---|---|
| Culture supernatant | 240 | 0.13 | 100 |
| Dialyzed solution after salting out with ammonium sulfate | 200 | 0.66 | 63 |
| Eluate from ion-exchange column chromatography | 140 | 7.3 | 58 |
| Eluate from hydrophobic column chromatography | 96 | 10 | 40 |

*CMM-forming enzyme

The finally purified enzyme preparation of CMM-forming enzyme was assayed for purify on gel electrophoresis using a 5-20% (w/v) gradient polyacrylamide gel and detected on the gel as a single protein band, i.e. a high purity preparation.

Experiment 5

Properties of CMM-forming Enzyme

Experiment 5-1

Molecular Weight

The purified enzyme preparation of CMM-forming enzyme, obtained by the method in Experiment 4, was subjected to SDS-PAGE and molecular weight of CMM-forming enzyme was measured comparing with molecular weight markers, commercialized by Bio-Rad Japan, Tokyo, Japan. It was revealed that CMM-forming enzyme of the present invention has a molecular weight of 72,000±20,000 daltons.

Experiment 5-2

Isoelectric Point

The purified enzyme preparation of CMM-forming enzyme, obtained by the method in Experiment 4, was subjected to polyacrylamide gel isoelectrofocusing containing 2% (w/v) "AMPHOLINE", a carrier ampholyte commercialized by Amersham Biosciences, Tokyo, Japan and isoelectric point of CMM-forming enzyme was measured compare with isoelectric point markers, commercialized by Amersham Biosciences, Tokyo, Japan. It was revealed that CMM-forming enzyme of the present invention has an isoelectric point (pI) of 3.6±0.5.

Experiment 5-3

Optimum Temperature and Optimum pH of the Enzyme Reaction

Figure 5:
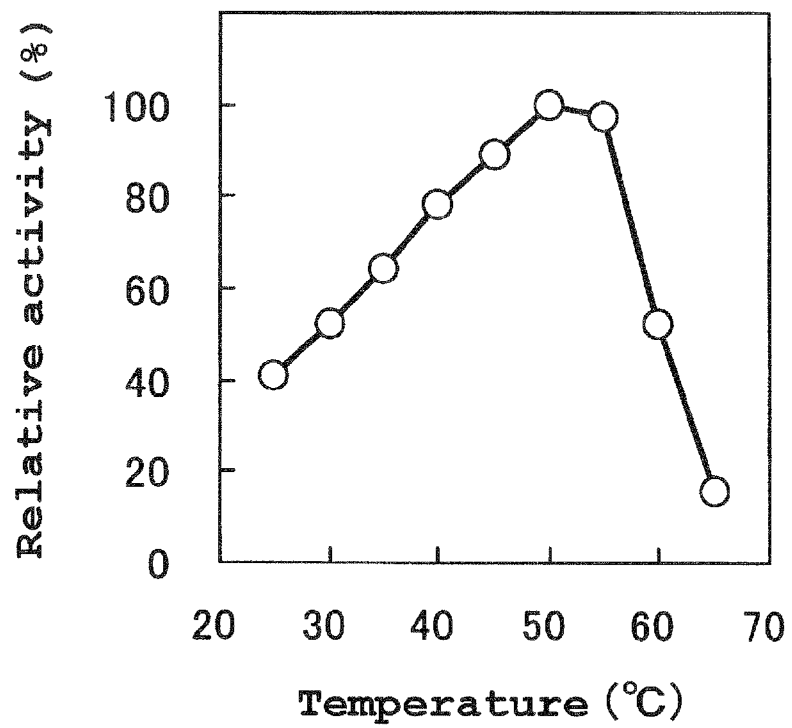
FIG. 5 shows the optimum temperature of CMM-forming enzyme.
Figure 6:
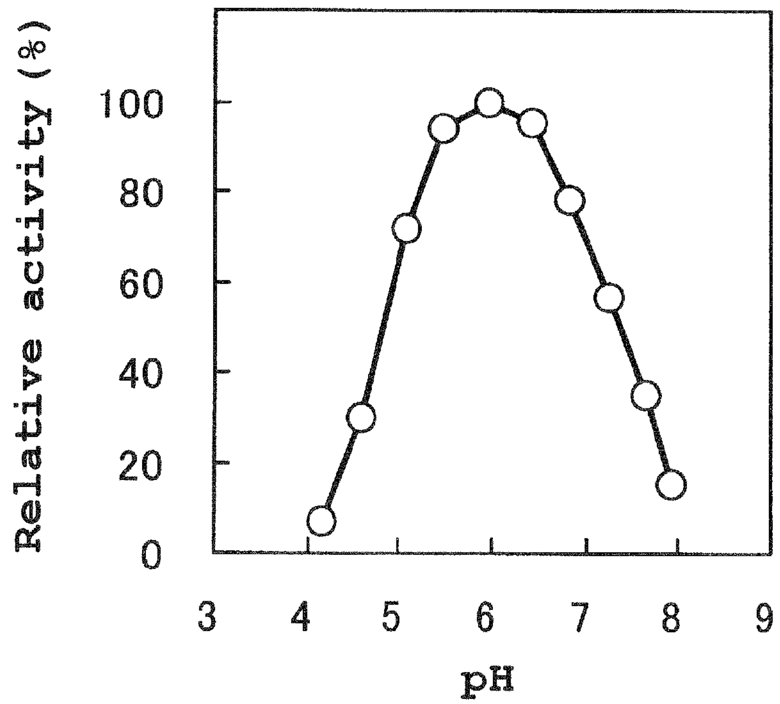
FIG. 6 shows the optimum pH of CMM-forming enzyme.

Effects of temperature or pH on the enzyme activity were investigated using the purified enzyme preparation of CMM-forming enzyme, obtained by the method in Experiment 4, by varying temperature and pH at the assay of the enzyme. The results are in FIG. 5 (Optimum temperature) and in FIG. 6 (Optimum pH), respectively. It was revealed that the optimum temperature of CMM-forming enzyme of the present invention was 50 to 55° C. when reacted at pH 6.0 for 30 min and the optimum pH was 5.5 to 6.5 when reacted at 40° C. for 30 min.

Experiment 5-4

Thermal Stability and pH Stability of the Enzyme

Figure 7:
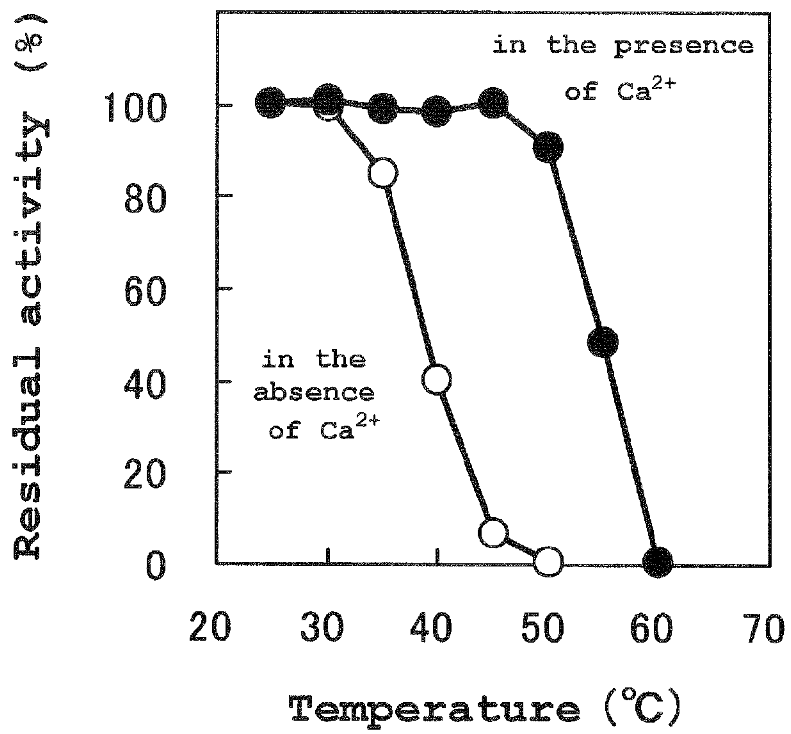
FIG. 7 shows the thermal stability of CMM-forming enzyme.
Figure 8:
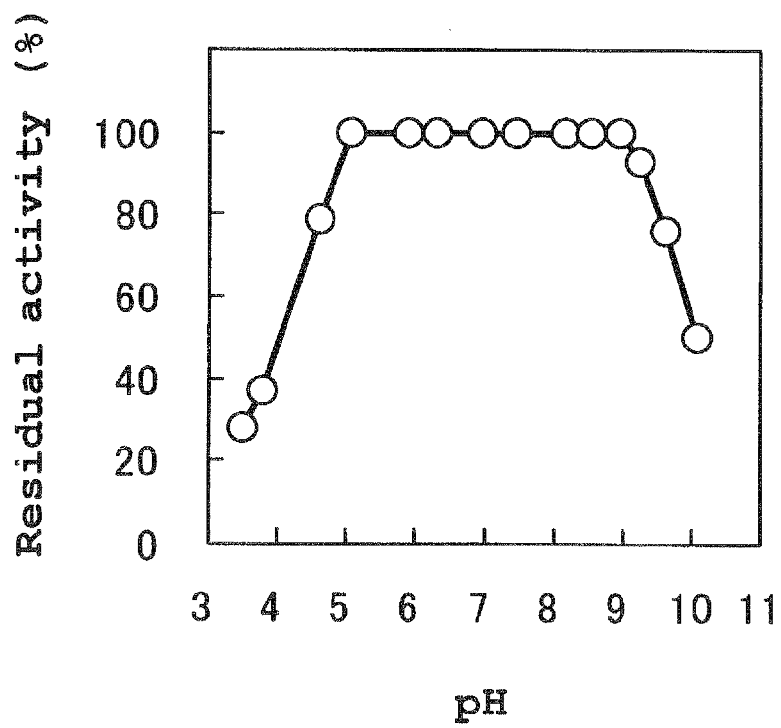
FIG. 8 shows the pH stability of CMM-forming enzyme.

Thermal stability and pH stability of the enzyme were investigated using the purified enzyme preparation of CMM-forming enzyme, obtained by the method in Experiment 4. Thermal stability of the enzyme was determined by the steps of incubating enzyme solution (10 mM acetate buffer, pH6.0) under various temperatures for 60 min in the absence or presence of 1 mM $CaCl_2$, cooling in water, and measuring the residual enzyme activity. pH Stability of the enzyme was determined by the steps of incubating enzyme solution in 100 mM buffer at various pHs, and at 4° C. for 24 hours, adjusting the pH to 6.0, and measuring the residual enzyme activity. The results are in FIG. 7 (Thermal stability) and in FIG. 8 (pH Stability), respectively. As is evident from the results in FIG. 7, CMM-forming enzyme of the present invention is stable up to 30° C. in the absence of $CaCl_2$, and to 50° C. in the presence of 1 mM $CaCl_2$. It was revealed that the thermal stability of the enzyme was improved in the presence of $Ca^{2+}$ ion. As is evident from the results in FIG. 8, it was revealed that CMM-forming enzyme of the present invention was stable in the range of pH 5.0 to 9.0.

Experiment 5-5

Effects of Metal Ions on the Enzyme Activity

Effects of metal ions on the enzyme activity were investigated using the purified enzyme preparation of CMM-forming enzyme, obtained by the method in Experiment 4, in the presence of 1 mM of various metal ions according to the assay method. The results are in Table 3.

TABLE 3

| Metal salt | Relative activity (%) | Metal salt | Relative activity (%) |
|---|---|---|---|
| None | 100 | $NiCl_2$ | 90 |
| $MgCl_2$ | 98 | $CuCl_2$ | 1 |
| $AlCl_3$ | 13 | $ZnCl_2$ | 73 |
| $CaCl_2$ | 99 | $SrCl_2$ | 90 |
| $MnCl_2$ | 97 | $BaCl_2$ | 90 |
| $FeCl_2$ | 95 | $HgCl_2$ | 2 |
| $FeCl_3$ | 32 | $PbCl_2$ | 36 |
| $CoCl_2$ | 95 | EDTA | 25 |

As is evident from the results in Table 3, it was revealed that CMM-forming enzyme activity was remarkably inhibited by $Cu^{2+}$ and $Hg^{2+}$, and also inhibited by $Al^{3+}$, $Fe^{3+}$ and $Pb^{2+}$. Further, it was revealed that the enzyme activity was also inhibited by EDTA, a chelating agent for metal ions.

Experiment 5-6

N-terminal Amino Acid Sequence

N-terminal amino acid sequence of the enzyme was determined using the purified enzyme preparation of CMM-forming enzyme, obtained by the method in Experiment 4, by "Model 429HT", a protein sequencer commercialized by Applied Biosystems Japan, Tokyo, Japan. As a result, it was revealed that the enzyme had the N-terminal amino acid sequence of SEQ ID NO:1, i.e., Asp-Pro-Thr-Thr-Ser.

Experiment 5-7

Partial Amino Acid Sequence

A part of the purified enzyme preparation of CMM-forming enzyme, obtained by the method in Experiment 4, was dialyzed against 10 mM Tris-HCl buffer (pH 9.0) at 4° C. for 18 hours, and the dialyzed solution was diluted with a fresh preparation of the same buffer to give a concentration of about one mg/ml. One milliliter of the diluted solution as was admixed with 20 μg of "LYSYL ENDOPEPTIDASE" commercialized by Wako Pure Chemicals, Ltd, Tokyo, Japan, and incubated at 30° C. for 16 hours to hydrolyze the enzyme protein. The resulting hydrolyzate was injected to "μ-BONDAPAK C18 column", having a diameter of 3.9 mm and a length of 150 mm, a HPLC column commercialized by Waters Chromatography Div., MILLIPORE Corp., Milford, USA, pre-equilibrated with 0.1% (v/v) trifluoroacetate containing 8% (v/v) acetonitrile, at a flow rate of 0.9 ml/min and at ambient temperature, and peptides were fractionated using a linear gradient of acetonitrile increasing from 8% (v/v) to 40% (v/v) in 0.1% (v/v) trifluoroacetate over 120 min. Peptide fragments eluted from the column were detected by monitoring the absorbance at a wavelength of 210 nm. Six kinds of peptide fragments eluted at a retention time of about 12 min, about 18 min, about 20 min, about 36 min, about 39 min and about 66 min were separately collected and amino acid sequences of these were analyzed according to the method in Experiment 5-6. These peptide fragments had amino acid sequences of SEQ ID NO:4 to 9.

Experiment 6

Cloning of a DNA Encoding CMM-forming Enzyme and Preparation of a Recombinant DNA Comprising the DNA and a Transformant A DNA encoding CMM-forming enzyme was cloned from *Arthrobacter globiformis* M6 (FERM BP-8448), and a self-replicable recombinant DNA containing the DNA was constructed. Successively, the nucleotide sequence of the DNA encoding the enzyme was determined and a transformant was also prepared.

Experiment 6-1

Preparation of Chromosomal DNA

A liquid culture medium consisting of 2.0% (w/v) of "PINE-DEX #4", a partial starch hydrolyzate commercialized by Matsutani Chemical Industries Co., Ltd., Hyogo, Japan, 1.0% (w/v) of "ASAHIMEAST", a yeast extract commercialized by Asahi Food & Healthcare Ltd., Tokyo, Japan, 0.1% (w/v) of dipotassium phosphate, 0.06% (w/v) of sodium phosphate dodeca-hydrate, 0.05% (w/v) of magnesium sulfate hepta-hydrate, and water was placed in 500 ml-Erlenmeyer flasks in a respective amount of 100 ml, sterilized by autoclaving at 121° C. for 20 min, cooled and inoculated with *Arthrobacter globiformis* M6, FERM BP-8448, followed by the cultivation under rotary-shaking conditions at 27° C. and 230 rpm for 24 hours.

The cells collected from the culture by centrifugation were suspended in TES buffer (pH 8.0), the suspended solution was admixed with lysozyme to give a concentration of 0.05% (w/v), and incubated at 37° C. for 30 min. After freezing the lysate at −80° C. for one hour, the lysate was added with TSS buffer (pH 9.0) and heated to 60° C. The solution was added with a mixture of TES buffer and phenol, and was vigorously shaken for five minutes in an ice bath, and the supernatant was collected by centrifugation. The supernatant was added twice volume of cold ethanol, and resulting precipitate was collected as a crude chromosomal DNA. The crude chromosomal DNA was dissolved in SSC buffer (pH 7.1), and admixed with 7.5 □g of ribonuclease and 125 □g of proteinase, and incubated at 37° C. for one hour. The chromosomal DNA was extracted from the reactant by adding chloroform/isoamylalcohol mixture, then, admixed with cold ethanol, and the resulting precipitate containing chromosomal DNA was collected. The purified chromosomal DNA, obtained according to the method described above, was dissolved in SSC buffer (pH 7.1) to give a concentration of about one mg/ml and frozen at −80° C.

Experiment 6-2

Preparation of a Recombinant DNA, pBMB1 and a Transformant, BMB1

One-tenth milliliter of purified chromosomal DNA solution, prepared in Experiment 6-1, was admixed with about 100 units of a restriction enzyme, Bam HI, and incubated at 37° C. for one hour to digest the chromosomal DNA. The resulting DNA fragments corresponding to about 3,000 to 6,000 base pairs were collected by agarose gel electrophoresis. A plasmid vector, "BLUESCRIPT II SK(+)®", commercialized by Stratagene Cloning System, was completely digested with a restriction enzyme, Bam HI by conventional method. A recombinant DNA was obtained by ligating 0.5 μg of the digested plasmid vector with about 5 μg of the DNA fragments prepared before by using a "DNA LIGATION KIT", commercialized by Takara Shuzo Co., Ltd., according to the method described in a document attached with the kit. Then, a gene library was prepared by transforming 100 μg portion of the competent cell, "EPICURIAN COLI XL2-BLUE", commercialized by Stratagene Cloning System, with the recombinant DNA by conventional competent cell method. The transformants, thus obtained as gene library, were inoculated into a fresh agar plate medium (pH 7.0) containing 10 g/L of tryptone, 5 g/L of yeast extract, 5 g/L of sodium chloride, 100 mg/L of ampicillin sodium salt, and 50 mg/L of 5-bromo-4-chloro-3-indolyl-β-galactoside, and incubated at 37° C. for 24 hours. About four thousand white colonies grown on the plate were transferred to and fixed on a nylon membrane, "HYBOND-N+", commercialized by Amasham Bioscience K.K. An oligonucleotide having a nucleotide sequence of "5'-GACGTSGTSCCSAACCA-CACSGCSGACTAC-3'" was chemically synthesized on the basis of an amino acid sequence of the fourth to 13th of SEQ ID NO:7, which disclosed by the method in Experiment 5-7. A synthetic DNA (probe 1) was obtained by labeling the oligonucleotide with radioisotope using [□-$^{32}$P] ATP and T4 polynucleotide kinase according to conventional method. Colonies showing remarkable hybridization with probe 1 were selected from the colonies fixed on a nylon membrane obtained before using conventional colony hybridization, and then five transformants were obtained.

Successively, an oligonucleotide having a nucleotide sequence of "5'-GACTGGGTSGACATGGGSTTC-GACGGSATC-3'" was chemically synthesized on the basis of an amino acid sequence of first to 10th of SEQ ID NO:8, and labeled with radioisotope by the same manner described above to make into a synthetic DNA (probe 2). The recombinant DNAs were collected from these five transformants by conventional method. A recombinant DNA showing remarkable hybridization with probe 2 was selected from the five recombinant DNAs using conventional southern hybridization. A transformant containing the selected recombinant DNA was named "BMB1".

Figure 9:
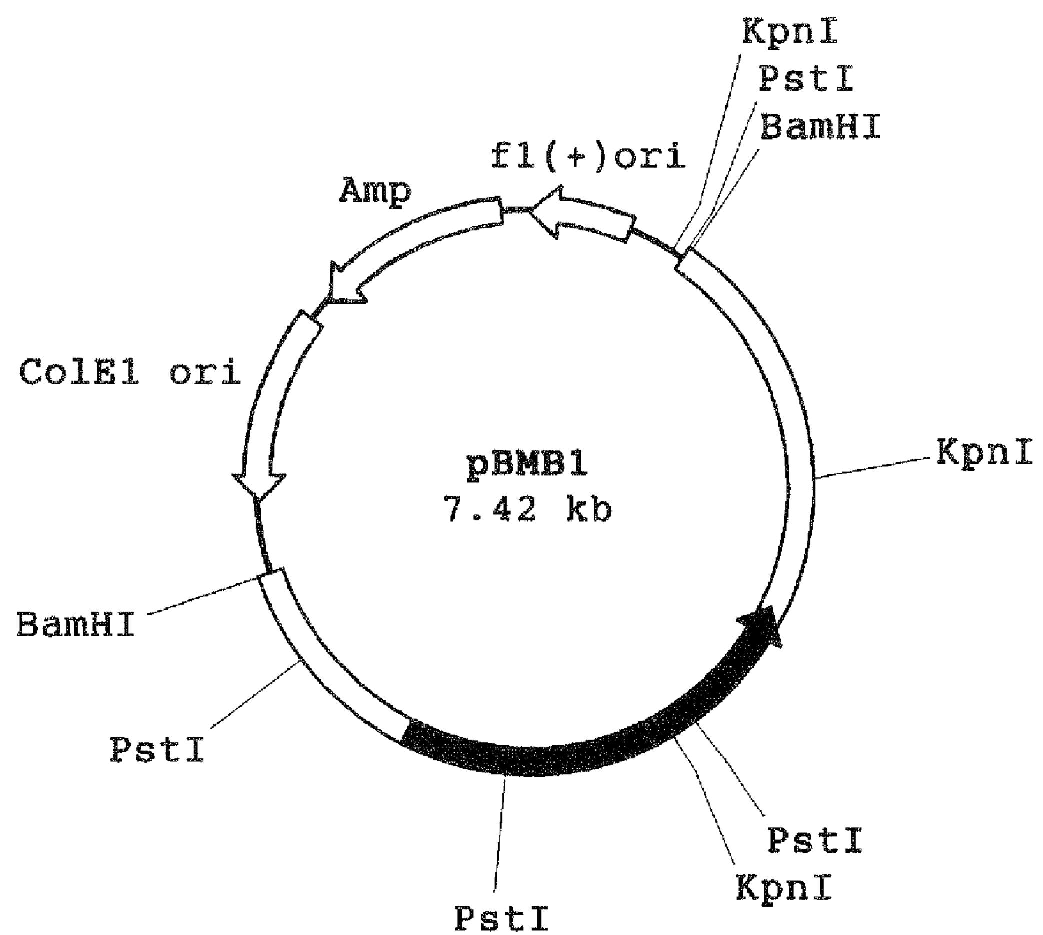
FIG. 9 shows a recombinant DNA, pBMB1, of the present invention.

According to conventional method, the transformant, BMB1 was inoculated into L-broth medium (pH 7.0) containing 100 μg/ml of ampicillin sodium salt, and cultured under rotary-shaking conditions at 37° C. for 24 hours. After completion of the culture, cells were collected by centrifugation from the culture, and the recombinant DNA was extracted from the cells by conventional alkaline-SDS method. When the nucleotide sequence of the recombinant DNA was analyzed by conventional dideoxy method, it was revealed that the recombinant DNA contained a DNA having the nucleotide sequence of SEQ ID NO:10, 4,467 base pairs, which originated from *Arthrobacter globiformis* M6 (FERM BP-8448). As shown in FIG. 9, in the recombinant DNA, the DNA was ligated at downstream of recognition site of a restriction enzyme, Bam HI. The amino acid sequence deduced from the nucleotide sequence is as shown in parallel in SEQ ID NO:10. The amino acid sequence was compared with amino acid sequences of CMM-forming enzyme of the present invention, i.e., the N-terminal amino acid sequence of SEQ ID NO:1 disclosed by the method in Experiment 5-6 and the internal partial amino acid sequences of SEQ ID NO:4 to 9 disclose by the method in Experiment 5-7. An amino acid sequence of SEQ ID NO:1 was completely identical with that of 41st to 45th of the amino acid sequence shown in parallel in SEQ ID NO:10. Amino acid sequences of SEQ ID NO:4, 5, 6, 7, 8, and 9 were completely identical with those of 418th to 426th, 405th to 417th, 323rd to 332nd, 164th to 190th, 241st to 265th, and 333rd to 362nd of the amino acid sequence shown in parallel in SEQ ID NO:10, respectively. These results indicate that CMM-forming enzyme of the present invention contains the amino acid sequence of SEQ ID NO:2, and that the enzyme is encoded by the DNA having the nucleotide sequence of SEQ ID NO:3 in the case of *Arthrobacter globiformis* M6 (FERM BP-8448). An amino acid sequence of the first to 40th of that shown in parallel in SEQ ID NO:10 was presumed to be a secretion signal sequence of the enzyme. According to the results described above, it was revealed that the precursor of the enzyme before secretion had the amino acid sequence shown in parallel in SEQ ID NO:10, and the amino acid sequence was encoded by the nucleotide sequence of SEQ ID NO:10. The recombinant DNA prepared and confirmed the nucleotide sequence as described above was named "pBMB1".

Experiment 7

Production of CMM-forming Enzyme by the Transformant

A liquid culture medium consisting of 5 g/L of "PINE-DEX #4", a partial starch hydrolyzate commercialized by Matsutani Chemical Industries Co., Ltd., Hyogo, Japan, 20 g/L of polypeptone, 20 g/L of yeast extract, 1 g/L of sodium phosphate dodeca-hydrate, and water was placed in a 500 ml-Erlenmeyer flask in a amount of 100 ml, sterilized by autoclaving at 121° C. for 20 min, and cooled. Then, the liquid medium was sterilely set to pH 7.0, and sterilely admixed with 10 mg of ampicillin sodium salt. A transformant, BMB1, obtained by the method in Experiment 6-2, was inoculated into the above liquid medium, and cultured at 27° C. for 48 hours under aeration-agitation conditions. Cells and supernatant were separately collected from the culture by conventional centrifugation. In the case of the cells, whole-cell extract was prepared by ultrasonic disruption. The ultrasonic disruption was carried out by suspending cells in 10 mM sodium phosphate buffer (pH 7.0) and disrupting cell suspension in a ice bath using a ultrasonic homogenizer, "Model UH-600", commercialized by MST Corporation, Aichi, Japan, and the resulting homogenate was used as a whole-cell extract.

CMM-forming enzyme activities of the culture supernatant and whole-cell extract, prepared as described above, were assayed, and those values were expressed in terms of the activities/ml-culture, respectively. As a control, CMM-forming enzyme activities of the culture supernatant and whole-cell extract of *E coli* XL-Blue, the host, were assayed after culturing the host and preparing the culture supernatant and whole-cell extract in the same manner. The results are in Table 4.

TABLE 4

| Strain | CMM-forming enzyme activity (units/ml-broth) | |
|---|---|---|
| | Culture supernatant | Whole cell extract |
| BMB1 (Present invention) | 0.00 | 0.05 |
| *E. coli* (Control) | 0.00 | 0.00 |

Note:
BMB1 and *E. coli*, in the Table, mean a transformant, BMB1, and *E. coli* XL2-Blue, respectively.

As is evident from the results in Table 4, it was revealed that the transformant, BMB1 produced CMM-forming enzyme of the present invention intracellularly. In the case of the host, *E. coli* XL2-Blue, no enzyme activity was detected from either of the culture supernatant and the whole-cell extract.

The whole-cell extract, obtained by the method in Experiment 7, was further purified by salting out, dialysis and successive column chromatographies on "DEAE-TOYOPEARL 650S" gel and "BUTYL-TOYOPEARL 650M" gel according to the methods in Experiment 4, and the purified enzyme preparation was analyzed according to the methods in Experiment 5. As the results, the molecular weight was about 72,000±20,000 daltons by SDS-polyacrylamide gel electrophoresis, the isoelectric point was about 3.6±0.5 by polyacrylamide gel isoelectrofocusing, the optimum temperature of CMM-forming enzyme activity was about 50 to 55° C., the optimum pH of the enzyme was about 5.5 to 6.5, the thermal stability was up to 30° C. in the absence of $CaCl_2$ and up to about 50° C. in the presence of 1 mM $CaCl_2$, and the pH stability was in the range of about pH 5.0 to about 9.0. These physicochemical properties were substantially identical to those of the enzyme prepared by the method in Experiment 4. The results described above indicate that CMM-forming enzyme of the present invention can be advantageously produced by recombinant DNA techniques and the productivity of the enzyme can be significantly improved by recombinant DNA techniques.

Experiment 8

Action on Various Saccharides

Substrate specificity of CMM-forming enzyme of the present invention was investigated using various saccharides as substrates. Substrate solutions were prepared by dissolving maltose, maltotriose, maltotetraose, maltopentaose, maltohexaose, maltoheptaose, neotrehalose, trehalose, kojibiose, nigerose, Nov. 16, 2007 isomaltose, isomaltotriose, panose, isopanose, maltitol, maltotriitol, α-, β- or γ-cyclodextrin, amylose, soluble starch, glycogen, pullulan or dextran into water. Each substrate solution was admixed with acetate buffer (pH 6.0) and $CaCl_2$ to give final concentrations of 20 mM and 1 mM, respectively. Then, each resulting substrate solution was further admixed with one unit/9-substrate, on a dry solid basis, of the purified preparation of CMM-forming enzyme, obtained by the method in Experiment 4. Substrate concentration was set to 2% (w/v) and followed by the enzyme reaction at 40° C. and pH 6.0 for 24 hours. Action and the specificity of the enzyme on these saccharides were confirmed by analyzing the reaction mixture before and after the reaction by TLC described in Experiment 1. The results are in Table 5.

TABLE 5

| Substrate | Action* | Substrate | Action* |
|---|---|---|---|
| Maltose | – | Panose | – |
| Maltotriose | + | Isopanose | – |
| Maltotetraose | +++ | Maltitol | – |
| Maltopentaose | +++ | Maltotriitol | – |
| Maltohexaose | +++ | α-Cyclodextrin | – |
| Maltoheptaose | +++ | β-Cyclodextrin | – |
| Neotrehalose | – | γ-Cyclodextrin | – |
| Trehalose | – | Amylose | +++ |
| Kojibiose | – | Soluble starch | +++ |
| Nigerose | – | Glycogen | ++ |
| Isomaltose | – | Pullulan | – |
| Isomaltotriose | – | Dextran | – |

*In comparison with before and after the reaction, the symbol, "–" means "Not changed". The symbol, "+" means "Spot of substrate is slightly decreased and other products are detected". The symbol, "++" means "Spot of substrate is markedly decreased and other products are detected". The symbol, "+++" means "Spot of substrate is virtually disappeared and other products are detected".

As is evident from the results in Table 5, CMM-forming enzyme of the present invention acts on maltotetraose, maltopentaose, maltohexaose, and maltoheptaose, and slightly on maltotriose among saccharides tested. Further, CMM-forming enzyme of the present invention acts on amylose, starch, and glycogen. From the results, it was revealed that the enzyme acted on α-1,4 glucans having a glucose polymerization degree of 3 or higher.

Experiment 9

Action Mechanism

Experiment 9-1

Product from Maltotetraose by the Enzyme Reaction

A substrate solution was prepared by mixing maltotetraose solution, acetate buffer (pH 6.0) and $CaCl_2$ to give final concentrations of 1% (w/v), 20 mM, and 1 mM, respectively. The substrate solution was admixed with one unit/g-substrate, on a dry solid basis, of CMM-forming enzyme, obtained by the method in Experiment 4, and followed by the enzyme reaction at 40° C. and pH 6.0. Aliquots were sampled from the reaction mixture with time and the reaction was stopped by keeping at 100° C. for 10 min. Saccharide compositions of the samples were measured by HPLC method. HPLC was carried out under the following conditions:

Column: "YMC Pack ODS-AQ303", produced by YMC Corporation, Tokyo, Japan;
Elute: Water;
Column temperature: 40° C.;
Flow rate: 0.5 ml/min; and
Detection: "RID-10A", a diffractometer produced by Shimadzu Corporation, Kyoto, Japan.

The results are in Table 6.

TABLE 6

| Reaction time | Saccharide composition (%) | | | | | | |
|---|---|---|---|---|---|---|---|
| (hours) | $G_2$* | CMM** | $G_4$* | MM*** | $G_6$* | X**** | Others |
| 0 | 0.0 | 0.0 | 97.3 | 0.0 | 0.0 | 0.0 | 2.7 |
| 1 | 9.0 | 2.6 | 69.5 | 0.5 | 3.9 | 11.3 | 1.8 |
| 2 | 15.6 | 6.6 | 51.7 | 0.9 | 5.6 | 14.0 | 2.6 |
| 4 | 22.8 | 12.5 | 35.5 | 1.8 | 5.4 | 14.7 | 3.5 |
| 8 | 31.7 | 21.3 | 19.1 | 3.8 | 4.1 | 10.8 | 5.7 |
| 16 | 36.3 | 25.6 | 10.9 | 6.9 | 2.5 | 8.2 | 6.5 |
| 24 | 38.7 | 28.6 | 6.9 | 9.6 | 1.2 | 7.1 | 6.1 |

*"$G_2$", "$G_4$" and "$G_6$" mean maltose, maltotetraose and maltohexaose, respectively.
**CMM means cyclic maltosylmaltose.
***MM means $6^2$-O-α-maltosylmaltose.
****"X" is revealed to be α-maltosylmaltotetraose (alias $6^4$-α-maltosylmaltotetraose) in Experiment 9-3 described later.

As is evident from the results in Table 6, it was revealed that maltose and Saccharide X were remarkably formed from substrate, maltotetraose at the initial stage of the enzyme reaction (one hour). Also, it was found that maltohexaose, CMM, and maltosylmaltose ($6^2$-α-maltosylmaltose, Non cyclic) were slightly formed at the stage. According to the progress of the reaction, maltose and CMM were remarkably accumulated and the amount of maltosylmaltose was slightly increased. While, it was revealed that contents of Saccharide X and maltohexaose were increased to the stage of four hours, but decreased later. According to the results, it was suggested that CMM-forming enzyme of the present invention acted on maltotetraose to form mainly maltose and Saccharide X, and acted on Saccharide X to form CMM with the progress of the reaction. Saccgaride X was considered to be an intermediate of CMM-forming reaction from maltotetraose. Since maltosylmaltose and maltohexaose were formed simultaneously, it was suggested that the enzyme catalyzed a transglycosylation by maltose unit and Saccharide X was a product of maltosyl-transferring reaction.

EXAMPLE 9-2

Isolation of Saccharide X

Isolation of Saccharide X which was considered to be an intermediate of CMM-forming reaction from maltotetraose was carried out. Two liters of 1% (w/v) maltotetraose aqueous solution was admixed with acetate buffer (pH 6.0) and $CaCl_2$ to give concentrations of 20 mM and 1 mM, respectively. The resulting substrate solution was admixed with one unit/g-substrate, on a dry solid basis, of the purified preparation of CMM-forming enzyme, obtained by the method in Experiment 4, and followed by the enzyme reaction at 40° C. and pH 6.0 for 4 hours. The enzyme reaction was stopped by keeping the reaction mixture at 100° C. for 10 min. After confirming that Saccharide X was not hydrolyzed by β-amylase by the preliminary test, the pH of the reaction mixture was adjusted to 5.5 and the resulting solution was admixed with five units/g-substrate, on a dry solid basis, of β-amylase, produced by Sigma-Aldrich Japan, Tokyo, Japan, and followed by the enzyme reaction at 50° C. for 16 hours to hydrolyze remaining maltotetraose into maltose. After stopping the reaction by keeping the reaction mixture at 100° C. for 10 min, insoluble substances were removed from the reaction mixture by filtration. The resulting filtrate was decolored and desalted using "DIAION WA30", an ion exchange resin commercialized by Mitsubishi Chemical Corporation, Tokyo, Japan, "DIAION SK-1B", a cation exchange resin commercialized by Mitsubishi Chemical Corporation, Tokyo, Japan, and "IRA 411S", an anion exchange resin commercialized by Organo Corporation, Tokyo, Japan. The resulting solution was filtrated and concentrated using an evaporator to make into a material for fractionation. The concentrate was subjected to preparative HPLC using "YMC-Pack ODS-A R355-15S-15 12A", a column produced by YMC Corporation, Tokyo, Japan, to purify Saccharide X and a preparation of Saccharide X with a purity of 99.3% or higher was obtained in a yield of about 6.7%, on a dry solid basis, from the reaction mixture prepared from maltotetraose.

Experiment 9-3

Structural Analysis of Saccharide X

Experiment 9-3-1

Test for Forming CMM

To 1% (w/v) aqueous solution of the purified preparation of Saccharide X, obtained by the method in Experiment 9-2, acetate buffer (pH 6.0) and $CaCl_2$ were mixed to give final concentrations of 20 mM and 1 mM, respectively. The resulting substrate solution was admixed with one unit/g-substrate, on a dry solid basis, of the purified preparation of CMM-forming enzyme, obtained by the method in Experiment 4, and followed by the enzyme reaction at 40° C. and pH 6.0 for 24 hours. After stopping the reaction by keeping the reaction mixture at 100° C. for 10 min, reaction products were analyzed by TLC and HPLC, described in Experiment 1. As a result, it was revealed that maltose and CMM were formed from Saccharide X as major products. It was confirmed that Saccharide X was an intermediate of CMM-forming reaction.

Experiment 9-3-2

Mass Spectrometry

The mass of Saccharide X was analyzed by the method in Experiment 2-1 using the purified preparation of Saccharide X, obtained by the method in Experiment 9-2. A sodium-added molecular ion with a mass of 1,013 was remarkably detected and the data revealed that the mass of Saccharide X was 990. The mass indicated that Saccharide X was constructed by six D-glucose molecules.

Experiment 9-3-3

Hydrolysis by Pullulanase

A digestion test was carried out by allowing pullulanase, commercialized by Hayashibara Biochemical Laboratories Inc., Okayama, Japan, to act on a 1% (w/v) aqueous solution of the purified preparation of Saccharide X, obtained by the method in Experiment 9-2. The substrate solution was admixed with one unit/g-substrate, on a dry solid basis, of pullulanase and followed by the enzyme reaction at 40° C. and pH 6.0 for 24 hours. After stopping the reaction by keeping the reaction mixture at 100° C. for 10 min, the reaction products were analyzed by TLC and HPLC, described in Experiment 1. As a result, maltose and maltotetraose were formed from Saccharide X. Therefore, it was revealed that Saccharide X had a structure of binding maltose molecule and maltotetraose molecule via the □-1,6 glucosidic linkage.

Experiment 9-3-4

Methylation Analysis

According to conventional method, the preparation of Saccharide X, obtained by the method in Experiment 9-2, was subjected to methylation analysis, and the resulting methylated products were analyzed by gas chromatography. The result is in Table 7.

TABLE 7

| Methylation product | Ratio |
|---|---|
| 2,3,4-Trimethylated product | 1.00 |
| 2,3,6-Trimethylated product | 4.04 |
| 2,3,4,6-Tetramethylated product | 0.85 |

As is evident from the result in Table 7, 2,3,4-trimethylated product, 2,3,6-trimethylated product, and 2,3,4,6-tetramethylated product were detected in a ratio of about 1:4:1. Therefore, it was revealed that, among six glucose molecules, one is glucose whose hydroxyl groups at C-1 and C-6 positions were involved in glucosidic linkages, four are glucoses whose hydroxyl groups at C-1 and C-4 positions were involved in glucosidic linkages, and one is glucose whose hydroxyl group at C-1 position was involved in glucosidic linkage. Further, from the result, it was revealed that the 1,6-glucosidic linkage existed at glucose residue at the non-reducing end in Saccharide X having a structure of binding maltose and maltotetraose via the □-1,6 glucosidic linkage.

From the results described above, it was revealed that Saccharide X, formed from maltotetraose by CMM-forming enzyme of the present invention, was an intermediate of CMM-forming reaction, and was a hexasaccharide having a structure of binding maltose with hydroxyl group at C-6 position of the non-reducing end glucose residue of maltotetraose via α-glucosidic linkage, i.e. α-maltosylmaltotetraose ($6^4$-α-maltosylmaltotetraose) represented by the structural formula I.

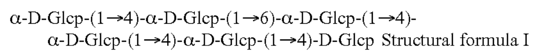

From the results described above, the mechanism of CMM-forming reaction by CMM-forming enzyme of the present invention was estimated as follows:

1) The enzyme acts on α-1,4 glucan having a glucose polymerization degree of 3 or higher as the substrate and forms 6-α-maltosylmaltooligosaccharide whose glucose polymerization degree is increased by two, having 6-α-maltosyl moiety at the non-reducing end, and maltooligosaccharide whose glucose polymerization degree is decreased by two by catalyzing an intermolecular 6-α-maltosyl transferring reaction to transfer a maltosyl moiety at the non-reducing end of the substrate to hydroxyl group at the C-6 position of the non-reducing end glucose of another α-1,4 glucan molecule.

(2) The enzyme further acts on 6-α-maltosylmalto-oligosaccharide and forms CMM having a structure of cyclo{>6)-α-D-glucopyranosyl-(1>4)-α-D-glucopyranosyl-(1>6)-α-D-glucopyranosyl-(1>4)-α-D-glucopyranosyl-(1>} and maltooligosaccharide whose glucose polymerization degree is decreased by four, by catalyzing an intermolecular α-maltosy transferring reaction to cyclize to form CMM.

(3) The enzyme slightly catalyzes an intermolecular 4-α-maltosyl transferring reaction and forms maltooligosaccharide whose glucose polymerization degree is increased by two and maltooligosaccharide whose glucose polymerization degree is decreased by two from a maltooligosaccharide.

Experiment 10

Formation of CMM from Various Substrates

Formation of CMM by the action of CMM-forming enzyme of the present invention was investigated using various saccharides as substrates. Maltotriose, maltotetraose, maltopentaose, maltohexaose, amylose, soluble starch, “PINEDEX #100”, a partial starch hydrolyzate commercialized by Matsutani Chemical Industries Co., Ltd., Hyogo, Japan, or glycogen from corn, commercialized by Q.P. Corporation, Tokyo, Japan, was prepared into a solution.

Each solution (concentration: 1.0% (w/v)) was admixed with acetate buffer (pH 6.0) and $CaCl_2$ to give final concentrations of 20 mM and 1 mM, further admixed with one unit/g-substrate, on a dry solid basis, of the purified preparation of CMM-forming enzyme, obtained by the method in Experiment 4, and followed by the enzyme reaction at 40° C. and pH 6.0 for 48 hours. The reaction was stopped by heating the reaction mixture at 100° C. for 10 min. After treating the reaction mixture with α-glucosidase and glucoamylase by the same manner in Experiment 1, the amount of CMM was determined by HPLC and CMM content of the reaction mixture was measured. The results are in Table 8.

TABLE 8

| Substrate | CMM content (%) |
|---|---|
| Maltotriose | 0.6 |
| Maltotetraose | 27.3 |
| Maltopentaose | 24.4 |
| Maltohexaose | 41.6 |
| Maltoheptaose | 36.6 |
| Amylose | 41.8 |
| Soluble starch | 31.4 |
| Partial starch hydrolyzate | 32.6 |
| Glycogen | 29.5 |

As is evident from the results in Table 8, CMM was formed from all substrate tested by the action of CMM-forming enzyme. In the case of using maltotriose as a substrate, CMM content was low about 0.6%. However, CMM content was the highest to about 42% in the case of using amylose as a substrate and higher in the case of using maltohexaose and maltoheptaose in that order. CMM was also formed from soluble starch, a partial starch hydrolyzate, and glycogen in contents of about 30%.

Experiment 11

Relationship of CMM-forming Reaction and the Reducing Power of the Reaction Products An aqueous solution containing 1.0% (w/v) of soluble starch was admixed with acetate buffer (pH 6.0) and $CaCl_2$ to give final concentrations of 20 mM and 1 mM, respectively. The resulting substrate solution was admixed with one unit/g-solid, on a dry solid basis, of the purified enzyme preparation of CMM-forming enzyme, obtained by the method in Experiment 4, and followed by the reaction at 40° C. and pH 6.0. A reaction mixture at the zero-time reaction was obtained by the steps of sampling the aliquot of the reaction mixture just after adding the enzyme, stopping the reaction by heating at about 100° C. for 10 min, and cooling the sample. Successively, aliquots of the reaction mixture were withdrawn at the reaction time of 1, 2, 3 and 4 hours, and the samples were immediately stopped the reactions by heating at about 100° C. for 10 min, and cooled to make into reaction mixtures reacted for 1, 2, 3, and 4 hours. The amount of reducing sugars and total sugars in the resulting reaction mixtures were measured by the Somogyi-Nelson method and Anthrone method. Reducing power of the reaction mixture was defined as the ratio of the amount of reducing sugars to the amount of total sugars and expressed in percentage. Further, the contents of CMM in the reaction mixtures were measured by the steps of treating the reaction mixtures with α-glucosidase and glucoamylase in the same manner in Experiment 1 and measuring the amounts of CMM by HPLC. The results are in Table 9.

TABLE 9

| Reaction time (hour) | Reducing power (%) | CMM content (%) |
|---|---|---|
| 0 | 0.3 | 0 |
| 1 | 0.3 | 4.7 |
| 2 | 0.4 | 8.4 |
| 3 | 0.5 | 11.2 |
| 4 | 0.5 | 13.7 |

As is evident from the results in Table 9, when CMM was formed by allowing CMM-forming enzyme of the present invention to act on soluble starch, it was revealed that the reducing powers of the reaction mixture were slightly increased by about 0.2% even when the contents of CMM were 10% or higher. These results indicate that CMM-forming enzyme of the present invention substantially catalyzes transferring and cyclizing reaction and hardly catalyzes hydrolytic reaction. It was also revealed that products with low reducing power can be obtained by lowering the reducing power of starches or starch hydrolyzates, i.e., the DE (dextrose equivalent) value before the reaction because the reducing power is hardly increased, when CMM is formed by allowing the enzyme to act on starches or starch hydrolyzates.

Experiment 12

Effect of the Addition of Isoamylase on the Formation of CMM

An aqueous solution containing 1% (w/v) of "PINEDEX #100", a partial starch hydrolyzate commercialized by Matsutani Chemical Industries Co., Ltd., Hyogo, Japan, was admixed with acetate buffer (pH 6.0) and $CaCl_2$ to give final concentrations of 20 mM and 1 mM, respectively. The resulting substrate solution was admixed with one unit/g-substrate, on a dry solid basis, of the purified preparation of CMM-forming enzyme, obtained by the method in Experiment 4, and zero, 125, 250, 500, 1,250 or 2,500 units/g-substrate, on a dry solid basis, of isoamylase commercialized by Hayashibara Biochemical Laboratories Inc., Okayama, Japan, and followed by the enzyme reaction at 40° C. and pH 6.0 for 48 hours. The reaction was stopped by heating the reaction mixture at 100° C. for 10 min. Successively, after treating the reaction mixture with α-glucosidase and glucoamylase by the same manner in Experiment 1, the amount of CMM was determined by HPLC and CMM content of the reaction mixture was measured. The results are in Table 10.

TABLE 10

| Amount of isoamylase (Units) | CMM content (%) |
|---|---|
| 0 | 32.2 |
| 125 | 40.1 |
| 250 | 40.1 |
| 500 | 40.9 |
| 1250 | 41.0 |
| 2500 | 41.7 |

As is evident from the results in Table 10, it was revealed that CMM content in the reaction mixture is increased by adding isoamylase.

Experiment 12

Effect of the DE Value of Liquefied Starch on the Formation of CMM

Cornstarch was prepared into 2% (w/w) suspension and admixed with calcium carbonate to give a concentration of 0.1% (w/w). After adjusting pH to 6.0, the resulting suspension was further admixed with "THERMAMYL 60L", an α-amylase commercialized by Novozymes Japan, Chiba, Japan, to give a concentration of 0.2, 0.4, 0.6, 1.0, 1.5, or 2.0% (w/w) per gram starch. These solutions were reacted at 95° C. for 10 min, autoclaved at 120° C., and immediately cooled to about 40° C. to obtain six kinds of liquefied starch solutions with DE values of 3.1 to 20.4, as shown in Table 11. Each liquefied starch solution was adjusted a final concentration of 1% (w/w), admixed with one unit/g-solid of the purified preparation of CMM-forming enzyme, obtained by the method in Experiment 4, and followed by the reaction at 40° C. and pH 6.0 for 48 hours. The reaction was stopped by boiling the reaction mixture for 10 min. To measuring the amount of CMM in the boiled reaction mixture, the reaction mixture was admixed with α-glucosidase and glucoamylase with the same manner in Experiment 1 and followed by the reaction. The CMM content in the resulting reaction mixture was obtained by measuring the amount of CMM by HPLC. The results are in Table 11.

TABLE 11

| Amount of α-amylase (w/w %/g-starch) | DE | CMM content (%) |
|---|---|---|
| 0.2 | 3.1 | 32.6 |
| 0.4 | 4.8 | 30.3 |
| 0.6 | 7.9 | 26.2 |
| 1.0 | 12.6 | 23.1 |
| 1.5 | 17.4 | 21.2 |
| 2.0 | 20.4 | 20.9 |

As is evident from the results in Table 11, CMM formation by CMM-forming enzyme of the present invention was influenced by the DE value of liquefied starch. It was revealed that CMM content in the reaction mixture was increased by decreasing DE value, in other word, decreased by increasing DE value. Particularly, it was revealed that DE value of the liquefied starch is preferable to, usually, about 20 or lower, desirably, about 8 or lower, more desirably, about 5 or lower.

Experiment 14

Preparation of Crystalline CMM

Sixteen liters of an aqueous solution, containing 1.25% (w/v) of amylose commercialized by Hayashibara Biochemical Laboratories Inc., Okayama, Japan, 20 mM of acetate buffer (pH 6.0), and 1 mM of $CaCl_{21}$ was admixed with one unit/g-solid of the purified preparation of CMM-forming enzyme, prepared by the method in Experiment 4, and followed by the reaction at 40° C. and pH 6.0 for 90 hours. The reaction was stopped by heating the reaction mixture at about 98° C. for 10 min. The resulting reaction mixture was treated with glucoamylase by the method described in Experiment 1, and reducing sugars in the reaction mixture were decomposed by the alkaline treatment. The resulting solution was decolored by filtration, desalted, filtrated, concentrated and dried in vacuo to obtain about 80.5 g, on a dry solid basis, of a powdery CMM product. The purity of CMM of the product was 98.9% by HPLC analysis.

The powdery CMM, 36 g, on a dry solid basis, was admixed with 144 g of water and completely dissolved by heating to about 90° C. After preserving the solution at about 25° C. for two days, crystalline substances were formed. The resulting suspension containing crystalline substances was filtrated and the crystalline substances on a filter were collected. Successively, the crystalline substances were washed with a small amount of water, collected, and dried under the conditions of an ambient temperature and a normal pressure to obtain 21.8 g of powdery crystals. The CMM crystal showed an extremely high purity of 99.9% or higher by HPLC analysis.

The powdery crystalline CMM was subjected to powdery X-ray diffraction analysis using "RAD-IIX", an X-ray diffractometer produced by Rigaku Corporation, Tokyo, Japan. As shown in FIG. 10, a powdery X-ray diffraction pattern having major diffraction angles (2θ) of 5.6°, 9.3°, 16.5°, and 27.1° was obtained. The moisture content of the powdery crystal was measured by Carl-Fisher method, revealing 12.8% (w/W). From the result, it was revealed that the crystal is a hydrous crystal which has five molecules of water to one molecule of CMM.

In addition, the powdery crystalline CMM was subjected to thermogravimetric analysis, and then a thermogravimetric curve shown in FIG. 11 was obtained. From the thermogravimetric curve, it was revealed that the weight corresponding to five molecules of water was decreased by elevating the temperature to about 100° C. and the weight caused by the thermal decomposition of intact CMM was decreased at the temperature of about 280° C. From these results, it was revealed that hydrous crystalline CMM of the present invention was converted in a normal pressure into anhydrate by releasing five molecules of water per one molecule of the crystal when the temperature was elevated to 100° C.

Experiment 15

Concentration of CMM in Saturated Aqueous Solution

To investigate the saturated concentration of CMM to water with a temperature of 25° C., 10 ml of water was put in a glass vessel attached with an airtight stopper, and then admixed with an excess amount, which can not be dissolved completely, of powdery hydrous crystalline CMM, obtained by the method in Experiment 14. Successively, the glass vessel was sealed, and the suspension was stirred two days with keeping the temperature at 25° C. to give a saturated solution. After removing the solid CMM by filtrating the saturated solution, the moisture content of the filtrate was measured by the drying loss method to determine the concentration of CMM in saturated solution. As a result, the saturated concentration of CMM to water with a temperature of 25° C. was revealed to be about 8.0% (w/w).

Experiment 16

Degree of Sweetness of CMM

A powdery hydrous crystalline CMM, obtained by the method in Experiment 14, was dissolved in water to make into a 5% (w/w) aqueous solution, and the resulting aqueous solution was used for testing the degree of sweetness. As controls, aqueous solutions containing sucrose (commercially available granulated sugar) was prepared by dissolving sucrose to give concentrations of 0.5 to 5% (w/w). By the sensory evaluation carried out by five panelists, the degree of sweetness of CMM was estimated to be about 20% of that of sucrose. It was revealed that CMM is a saccharide with a low sweetness.

Experiment 17

Thermal Stability of CMM

A powdery hydrous crystalline CMM was dissolved in water for preparing an aqueous solution containing 7% (w/v) of CMM. Eight milliliters each of the resulting solution was pored into a glass tube, sealed closely, and then heated at 120° C. for 30 to 90 min. After cooling the solution, the degree of coloring of the solution was measured. Further, the purity of CMM in the solution was measured by HPLC. The degree of coloring was defined as an absorbance at 480 nm using a 1 cm-cell. The results are in Table 12.

TABLE 12

| Heating time (min) | Degree of coloring (A480 nm) | Purity (%) |
|---|---|---|
| 0 | 0 | 100 |
| 30 | 0 | 100 |
| 60 | 0 | 100 |
| 90 | 0 | 100 |

As is evident from the results in Table 12, aqueous solutions of CMM were not colored, and the purities of CMM were not decreased even in the case of heating to a high temperature, 120° C. It was revealed that CMM is stable under the heating condition.

Experiment 18 pH Stability of CMM

The powdery hydrous crystalline CMM, obtained by the method in Experiment 14, was dissolved in various buffers (20 mM) to make into eight kinds of aqueous solutions containing 4% (w/v) of CMM, adjusted to pH 2 to 9, as shown in Table 13. Eight milliliters of each solution was put in a glass tube, sealed and then heated at 100° C. for 24 hours. After cooling the solution, the degree of coloring and the purity of CMM were measured in the same manner in Experiment 17. The results are in Table 13.

TABLE 13

| pH | Kind of buffer | Degree of coloring (A480 nm) | Purity (%) |
|---|---|---|---|
| 2.0 | Acetate | 0 | 93 |
| 3.0 | Acetate | 0 | 100 |
| 4.0 | Acetate | 0 | 100 |
| 5.0 | Acetate | 0 | 100 |
| 6.0 | Tris-HCl | 0 | 100 |
| 7.0 | Tris-HCl | 0 | 100 |
| 8.0 | Tris-HCl | 0 | 100 |
| 9.0 | Ammonium | 0 | 100 |

As is evident from the results in Table 13, aqueous solutions of CMM were not colored in a wide pH range of 2 to 9 even in the case of heating a high temperature, 100° C. for 24 hours. Although the purity of CMM was slightly decreased by the decomposition at pH 2, no decomposition was observed in a pH range of 3 to 9. It was revealed that CMM is extremely stable even in the case of boiling under wide pH conditions.

Experiment 19

Amino-carbonyl Reaction

The powdery hydrous crystalline CMM, obtained by the method in Experiment 14, was dissolved in water. The resulting solution was admixed with commercially available super high-grade glycine and phosphate buffer to make into an aqueous solution containing 2.5% (w/v) of CMM, 0.5% (w/v) glycine, and 50 mM phosphate buffer (pH 8.0). As a control, an aqueous solution containing maltose and glycine was prepared in the same manner using maltose except for the powdery hydrous crystalline CMM. Four milliliters each of the solution was put in a glass tube, sealed and then heated at 100° C. for 30, 60, or 90 min. After cooling the solutions, the degrees of coloring of the solutions were measured to estimate the degree of amino-carbonyl reaction. The degree of coloring was defined as an absorbance at 480 nm using a 1 cm-cell. The results are in Table 14.

TABLE 14

| Heating time (min) | Degree of coloring (A480 nm) | |
|---|---|---|
| | CMM | Maltose (Control) |
| 0 | 0.00 | 0.00 |
| 30 | 0.00 | 0.02 |
| 60 | 0.00 | 0.08 |
| 90 | 0.00 | 0.17 |

As is evident from the results in Table 14, maltose solution, the control of the test, caused browning by heating in the presence of glycine. While, the solution containing CMM of the present invention showed no browning by heating in the presence of glycine. It was revealed that CMM is a stable saccharide which hardly causes amino-carbonyl reaction (Maillard reaction).

Experiment 20

Amino-carbonyl Reaction

The powdery hydrous crystalline CMM, obtained by the method in Experiment 14, and commercially available polypeptone commercialized by Nihon Pharmaceutical Co., Ltd., Tokyo, Japan, were dissolved in deionized water to make into an aqueous solution containing 5% (w/v) of CMM and 5% (w/v) of polypeptone. As a control, an aqueous solution containing maltose and polypeptone was prepared in the same manner using maltose except for the powdery hydrous crystalline CMM. Four milliliters each of the solution was put in a glass tube, sealed and then heated at 120° C. for 30, 60, or 90 min. After cooling the solutions, the degrees of coloring of the solutions were measured to estimate the degree of amino-carbonyl reaction. As a blank test, a solution containing polypeptone only was heated in the same manner. The degree of coloring was defined as an absorbance at 480 nm using a 1 cm-cell after subtracting the absorbance of the blank test. The results are in Table 15.

TABLE 15

| Heating time (min) | Degree of coloring (A480 nm) | |
|---|---|---|
| | CMM | Maltose (Control) |
| 0 | 0.00 | 0.00 |
| 30 | 0.00 | 0.10 |
| 60 | 0.00 | 0.30 |
| 90 | 0.00 | 0.62 |

As is evident from the results in Table 15, maltose solution, the control of the test, caused browning by heating in the presence of polypeptone. While, the solution containing CMM of the present invention showed no browning by heating in the presence of polypeptone. It was revealed that CMM is a stable saccharide which hardly causes amino-carbonyl reaction (Maillard reaction).

Experiment 21

Clathrating Action of CMM

The powdery hydrous crystalline CMM, obtained by the method in Experiment 14, was dissolved in deionized water to make into an aqueous solution containing 8% (w/v) of CMM. One hundred grams of the aqueous solution was admixed with 1.2 g of methanol, 1.7 g of ethanol, or 2.2 g of acetic acid as flavor components for allowing CMM to clathrate the flavor components. Successively, each solution was filtrated, and the resulting filtrate was freeze-dried to remove unclathrated flavor component. As a control, "ISOELITE P", a mixture of branched cyclodextrins commercialized by Maruha Corporation, Tokyo, Japan, which has been known to have a clathrating activity, was tested by the same procedure. In order to measure the amount of flavor component clathrated in the freeze-dried powder, 1 g of each freeze-dried powder was dissolved in 5 ml of water and admixed with 5 ml of diethylether to extract the flavor component, and the extraction was repeated once more. The amount of the extracted flavor component in diethylether was measured by gas-chromatography. The results are in Table 16.

TABLE 16

| Objective flavor component | Amount of flavor component clathrated (mg/g-freeze-dried powder) CMM | Branched CD* |
|---|---|---|
| Methanol | 4.30 | 3.23 |
| Ethanol | 4.20 | 8.67 |
| Acetic acid | 30.55 | 38.14 |

*CD: Cyclodextrin

As is evident from the results in Table 16, it was revealed that CMM has a clathrating activity. The strength of the activity of CMM was about 1.3-folds, 0.5-fold, and 0.8-fold in the cases of methanol, ethanol, and acetic acid, respectively, on a weight basis, in comparison with those of branched cyclodextrin.

Experiment 22

Digestibility of CMM

According to the method of Okada et al., described in *Journal of Japanese Society of Nutrition and Food Sciences*, vol. 43, 23-29 (1990), the digestibility of CMM by salivary α-amylase, artificial gastric juice, pancreas amylase, and small intestinal enzymes were investigated using the powdery hydrous crystalline CMM, obtained by the method in Experiment 14. Maltitol, which has been known as a hardly digestive saccharide, was used as a control. The results are in Table 17.

TABLE 17

| Digestive enzyme | Degradation rate (%) CMM | Maltitol (Control) |
|---|---|---|
| Salivary α-amylase | 0 | 0 |
| Artificial gastric juice | 0 | 0 |
| Pancreas α-amylase | 0 | 0 |
| Small intestinal enzymes | 0 | 4 |

As is evident from the results in Table 17, CMM was not digested at all by either of salivary amylase, artificial gastric juice, pancreas amylase and small intestinal enzymes. It was revealed that CMM is one of hardly digestive saccharides.

Experiment 23

Test for Fermentability of CMM

According to the method of Oku et al., described in *Journal of Nutritional Science and Vitaminology*, vol. 37, 529-544 (1991), the fermentability of CMM by rat cecal contents were investigated using the powdery hydrous crystalline CMM, obtained by the method in Experiment 14. The cecal contents was collected under an anaerobic condition by killing a Wister-rat under anesthesia and suspended into 4-folds by volume of 0.1 M sodium bicarbonate aqueous solution, and then used for the test. CMM was added to the cecal contents by about 7% (w/w) of the weight of the cecal contents. The amounts of CMM at just after mixing and after 12 hours were determined by gas-chromatography. As the results, the concentrations of CMM in the cecal contents just after adding and after 12 hours were 68.5 mg/g-cecal contents and 63.0 mg/g-cecal contents, respectively. About 92% of CMM was not fermented and remained. It was revealed that CMM is one of hardly fermentable saccharides.

Experiment 24

Acute Toxicity Test

By using mice, CMM obtained by the method in Experiment 14 was orally administrated to the mice for its acute toxicity test. As a result, it was revealed that CMM is a safe substance with a relatively low toxicity, and that no mouse died even when administrated with it at the highest possible dose. Though not so accurate, the value of $LD_{50}$ of CMM was 5 g/kg-mouse weight or higher.

From the above results in Experiments 22 to 24, it was revealed that CMM can be advantageously used for diet sweeteners, excipient for high-sweetness sweetener, thickener for diet foods and beverages, fillers, excipients, dietary fibers, materials for substitute of fats, etc., as a non- or low calorie edible material because it is hardly digested and adsorbed when orally administrated.

The followings explain the process for producing CMM or saccharide compositions comprising the same in Examples 1 to 6, and compositions comprising CMM or saccharide compositions comprising the same in Examples 7 to 23.

EXAMPLE 1

According to the method in Experiment 3, *Arthrobacter globiformis* M6 (FERM BP-8448) was cultivated to obtain the seed culture. Successively, a liquid medium containing 3.0% (w/v) of "PINE-DEX #100", a partial starch hydrolyzate commercialized by Matsutani Chemical Industry Co., Ltd., Hyogo, Japan), 3.6% (w/v) of "HI-NEUTE SMS", soy protein oligopeptides commercialized by Fuji Oil Co., Ltd., Osaka, Japan, 0.1% (w/v) of dipotassium phosphate, 0.06% (w/v) of sodium phosphate dehydrate, 0.05% (w/v) of magnesium sulfate heptahydrate, 0.3% (w/v) of calcium carbonate, and water was placed in a 30-L fermenter in an amount of about 20 L, sterilized by heating, and cooled to 27° C. Then, 1% (v/v) of the liquid medium of the seed culture was inoculated into the liquid medium, and the bacteria was cultured with keeping a temperature at 27° C. and pH at 5.5 to 8.0 for 96 hours under aeration-agitation conditions. After completion of the cultivation, cells were removed by filtrating with SF-membrane and about 18 L of the resulting culture filtrate was collected. Further, the filtrate was concentrated using a UF-membrane and about 1 L of a concentrated enzyme solution, containing 3.8 units/ml of CMM-forming enzyme activity, was obtained.

EXAMPLE 2

A potato starch was prepared into a 1% (w/v) starch suspension, admixed with calcium carbonate to give a final concentration of 1 mM, adjusted to pH 6.0, and then gelatinized by heating at 95° C. for about 20 min. After cooling the resulting substrate solution to about 40° C., the concentrated enzyme solution containing CMM-forming enzyme, obtained by the method in Example 1, was admixed with the substrate solution to give a ratio of 0.26 ml (about one unit)/g-dry solid of starch, and followed by the enzymatic reaction at pH 6.0 and 40° C. for 48 hours. After keeping to 95° C. for 30 min, the reaction mixture was cooled and filtrated. According to conventional manner, the resulting filtrate was decolored with activated charcoal, desalted and purified with ion exchangers in H— and OH— forms. Then, the purified solution was concentrated to give a concentration of 65% (w/v) and a syrup containing CMM was obtained in a yield of about 90%, on a dry solid basis. The syrup contained, on a dry solid basis, 31.4% (w/w) of CMM, 2.2% (w/w) of maltose, 1.5% (w/w) of maltotriose, and 65.9% (w/w) of other saccharides. Since the product has a relatively low reducing power, mild sweetness, adequate viscosity, moisture-retaining ability, and clathrating activity, it can be advantageously used in various compositions such as foods and beverages, cosmetics, and pharmaceuticals as a sweetener, taste-improving agent, flavor-improving agent, quality-improving agent, syneresis-preventing agent, stabilizer, discoloration-preventing agent, excipient, clathrating agent, and base for powderization.

EXAMPLE 3

A tapioca starch was prepared into a 1% (w/v) starch suspension, admixed with calcium carbonate to give a concentration of 0.1% (w/v), adjusted to pH 6.5, and admixed with 0.2%/g-starch of "THERMAMYL 60 L", an α-amylase commercialized by Novo Industries A/S, Copenhagen, Denmark, and then incubated at 95° C. for 10 min. After autoclaving at 120° C. for 20 min, the reaction mixture was cooled rapidly to about 40° C. to make into a liquefied starch solution with a DE of about 3. The liquefied starch solution was admixed with 0.26 ml (about one unit)/g-dry solid starch of the concentrated enzyme solution containing CMM-forming enzyme, obtained by the method in Example 1, and 1,000 units/g-dry solid starch of isoamylase commercialized by Hayashibara Biochemical Laboratories Inc., Okayama, Japan, and followed by the enzymatic reaction at pH 6.0 and 40° C. for 48 hours. After heating to 95° C. for 30 min, the reaction mixture was cooled and filtrated. According to conventional manner, the resulting filtrate was decolored with activated charcoal, desalted and purified with ion exchangers in H— and OH— forms. Then, the purified solution was concentrated to give a concentration of 60% (w/v) and a syrup containing 41.1% (w/w), on a dry solid basis, of CMM was obtained. The syrup as a saccharide solution was subjected to a column chromatography using "AMBERLITE CR-1310" (Na-form), a strongly acidic cation-exchange resin commercialized by Organo Corporation, Tokyo, Japan. The resin was packed into four jacketed stainless steel columns having a diameter of 5.4 cm, which were then cascaded in series to give a total gel bed depth of 20 m. Under the conditions of keeping the inner column temperature at 60° C., the saccharide solution was fed to the columns in a volume of 5% (v/v) and fractionated by feeding to the columns hot water heated to 60° C. at an SV (space velocity) of 0.13 to obtain high CMM content fractions. While monitoring the saccharide composition of elute by HPLC, and then the low molecule fractions including the saccharide fraction comprising CMM were collected and the fractions were purified, concentrated and spray-dried. As a result, a powdery product comprising CMM was obtained in a yield of about 54%, on a dry solid basis. The product contained, on a dry solid basis, 63.2% of CMM, 7.4% of maltose, 6.2% of maltotriose, and 23.2% of other saccharides. Since the product has a relatively low reducing power, mild sweetness, adequate viscosity, moisture-retaining ability, and clathrating activity, it can be advantageously used in various compositions such as foods and beverages, cosmetics, and pharmaceuticals as a sweetener, taste-improving agent, flavor-improving agent, quality-improving agent, syneresis-preventing agent, stabilizer, discoloration-preventing agent, excipient, and clathrating agent.

EXAMPLE 4

A corn starch was prepared into a 1% (w/v) starch suspension, admixed with calcium carbonate to give a concentration of 0.1% (w/v), adjusted to pH 6.0, and admixed with 0.2%/g-starch of "NEOSPITASE", an α-amylase commercialized by Nagase ChemteX Corporation, Osaka, Japan, and then incubated at 85° C. to 95° C. for 20 min. After autoclaving at 120° C. for 20 min, the reaction mixture was cooled rapidly to about 40° C. to make into a liquefied starch solution with a DE of about 3. The liquefied starch solution was admixed with 0.26 ml (about one unit)/g-dry solid starch of the concentrated enzyme solution containing CMM-forming enzyme, obtained by the method in Example 1, and 1,000 units/g-dry solid starch of isoamylase commercialized by Hayashibara Biochemical Laboratories Inc., Okayama, Japan, and followed by the enzymatic reaction at pH 6.0 and 40° C. for 48 hours. After heating to 95° C. for 30 min, the reaction mixture was cooled to about 50° C. and adjusted to pH 5.0. Then, the reaction mixture was admixed with 100 units/g-starch of "GLUCOZYME", a glucoamylase commercialized by Nagase ChemteX Corporation, Osaka, Japan, and followed by the enzyme reaction at pH5.0 and 50° C. for 16 hours. After heating the reaction mixture to 95° C. and keeping for 30 min, it was cooled and filtrated. According to conventional manner, the resulting filtrate was decolored with activated charcoal, desalted and purified with ion exchangers in H— and OH— forms. Then, the purified solution was concentrated to give a concentration of 60% (w/v) and a syrup comprising CMM was obtained in a yield of about 95%, on a dry solid basis. The product contained, on a dry solid basis, 42.6% (w/w) of CMM, 53.0% (w/w) of glucose, and 4.4% (w/w) of other saccharides. Since the product has a mild sweetness, adequate viscosity, moisture-retaining ability, and clathrating activity, it can be advantageously used in various compositions such as foods and beverages, cosmetics, and pharmaceuticals as a sweetener, taste-improving agent, flavor-improving agent, quality-improving agent, syneresis-preventing agent, stabilizer, discoloration-preventing agent, excipient, clathrating agent, and base for powderization.

EXAMPLE 5

According to conventional method, the syrup comprising CMM, obtained by the method in Example 4, was hydrogenated to convert reducing saccharide into sugar alcohols. The resulting reaction mixture was purified, concentrated, dried in vacuo, and pulverized and a powdery product comprising CMM was obtained in a yield of about 90%, on a dry solid basis. The product contained, on a dry solid basis, 42.6% of CMM, 53.2% of sorbitol, and 4.2% of other sugar alcohols. Since the product substantially shows no reducing power, hardly causes amino-carbonyl reaction, and has a low reducing power, mild sweetness, adequate viscosity, moisture-retaining ability, and clathrating activity, it can be advantageously used in various compositions such as foods and beverages, cosmetics, and pharmaceuticals as a sweetener, taste-improving agent, flavor-improving agent, quality-improving agent, syneresis-preventing agent, stabilizer, discoloration-preventing agent, excipient, and clathrating agent.

EXAMPLE 6

In order to increase the content of CMM, the syrup comprising CMM, obtained by the method in Example 4, was subjected to a column chromatography using the strongly acidic cation exchange resin in a salt form according to the method in Example 3. CMM high content fractions were collected and purified, and a CMM high content solution, comprising CMM in a content of about 90%, on a dry solid basis, was obtained in a yield of about 40%, on a dry solid basis. The solution was concentrated and continuously crystallized to make into a massecuite. The resulting massecuite was centrifuged using a basket-type centrifugal machine to remove remaining syrup. The resulting crystal was washed with a small amount of water and dried through a hot air, and hydrous crystalline CMM in a high purity was obtained in a yield of about 25%, on a dry solid basis. The product is a high purity hydrous crystalline CMM with a purity of 99% or higher. The product shows extremely low reducing power and hardly causes amino-carbonyl reaction. Further, the product shows no hygroscopicity, and good handling. Since the product has a mild sweetness, adequate viscosity, moisture-retaining ability, clathrating activity, and low digestibility, it can be advantageously used in various compositions such as foods and beverages, cosmetics, and pharmaceuticals, and industrial reagents and chemical materials as a sweetener, material of low calorie foods, taste-improving agent, flavor-improving agent, quality-improving agent, syneresis-preventing agent, stabilizer, discoloration-preventing agent, excipient, clathrating agent, and base for powderization.

EXAMPLE 7

Sweetener

To 0.8 part by weight of hydrous crystalline CMM, obtained by the method in Example 6, 0.2 part by weight of "TREHA®", hydrous crystalline trehalose commercialized by Hayashibara Shoji Inc., Okayama, Japan, 0.01 part by weight of "αG-SWEET", α-glycosyl-stevioside commercialized by Toyo Sugar Refining Co., Ltd, Tokyo, Japan, and 0.01 part by weight of "ASPERTAME", L-aspartyl-L-phenylalanine-methyl-ester commercialized by Ajinomoto Co., Inc., Tokyo, Japan, were mixed to homogeneity and granulated using a granulator to make into a sweetener in a granule form. The product has a good sweetness and shows about 2-folds higher sweetness than sucrose. The product has substantially no or low calorie because CMM is a low-digestive and less fermentable saccharide. Since the product is stable with no fear of deterioration under the preservation at ambient temperature, it can be advantageously used as a sweetener with a high quality, low calorie, and low-cariogenicity.

EXAMPLE 8

Hard Candy

Fifty parts by weight of a syrup comprising CMM, obtained by the method in Example 4, was admixed with 100 parts by weight of sucrose solution with a sucrose concentration of 55% (w/v) with heating. Then, the mixture was concentrated under a reduced pressure to give a moisture content of less than 2%. The resulting concentrate was admixed with 0.6 part by weight of citric acid and suitable amounts of lemon flavor and coloring, shaped into hard candy according to conventional method. The product shows a satisfactory non-adhesion, taste, flavor, and hardly causes the crystallization of sucrose. The product is a high quality hard candy with low hygroscopicity and no fluidity.

EXAMPLE 9

Chewing Gum

Three parts by weight of gum base was softened by heating and melting, and then admixed with two parts by weight of anhydrous maltitiol, two parts by weight of xylitol, two parts by weight of hydrous crystalline CMM obtained by the method in Example 6, one part by weight of hydrous crystalline trehalose, and suitable amounts of flavor and colorings. The mixture was kneaded by a roll, shaped and packed to make into chewing gum. Since the product has a satisfactory texture, taste, and flavor, it is preferable as a chewing gum with a low-cariogenicity, and low calorie.

EXAMPLE 10

Sweetened Condensed Milk

Four parts by weight of a syrup comprising CMM, obtained by the method in Example 2, and two parts by weight of sucrose were dissolved in 100 parts by weight of material milk. The resulting mixture was sterilized by heating with a plate heater, concentrated to give a concentration of 70%, and then packed in a can to make into a product. Since the product has a mild sweetness and good flavor, it can be advantageously used for seasoning fruits, coffee, cocoa, black tea, and the like.

EXAMPLE 11

Lactic Acid Bacteria Beverage

One hundred seventy-five parts by weight of skim milk, 100 parts by weight of a powdery product comprising CMM, obtained by the method in Example 3, and "NYUKA-OLIGO", a lactosucrose high content powder commercialized by Hayashibara Shoji Inc., Okayama, Japan, were dissolved into 1,500 parts by weight of water, and then the resulting mixture was sterilized at 65° C. for 30 min. After cooling the mixture to 40° C., 30 parts by weight of a lactic acid bacterium was inoculated to the mixture as a starter according to conventional method, and cultured at 37° C. for eight hours to obtain a lactic acid bacteria beverage. The product has a satisfactory flavor and keeps the lactic acid bacterium stably because it comprises oligosaccharides and CMM. Further, the product is preferably used as a lactic acid bacteria beverage having a growth-promoting activity for bifidobacteria and a function-regulating activity for intestine.

EXAMPLE 12

Powdery Juice

To 33 parts by weight of a powdery orange juice, produced by a spray-drying method, 50 parts by weight of powdery hydrous crystalline CMM, obtained by the method in Example 6, parts by weight of anhydrous crystalline maltitol, 0.65 part by weight of anhydrous citric acid, 0.1 part by weight of malic acid, 0.2 part by weight of 2-O-α-glucosyl-L-ascorbic acid, 0.1 part by weight of sodium citrate, 0.5 part by weight of pullulan, and suitable amount of powdery flavor were mixed with stirring and the resulting powdery mixture was pulverized to make into a fine powdery product. Then, the powdery product was subjected to a fluidized bed granulator and its exhaust temperature was set to 40° C. A suitable amount of a syrup comprising CMM, obtained by the method in Example 2, was sprayed on the powdery product and granulated for 30 min and the resulting product was weighted and packed to make into a product. The product is a powdery juice with a fruit-juice content of about 30%. Since the product shows no strange taste and smell, it has a high quality and commercial value as a low-calorie juice.

EXAMPLE 13

Custard Cream

One hundred parts by weight of corn starch, 100 parts by weight of a syrup comprising CMM, obtained by the method in Example 2, 60 parts by weight of hydrous crystalline trehalose, 40 parts by weight of sucrose, and one part by weight of sodium chloride were mixed well, and then 280 parts by weight of whole egg was further admixed with the mixture. Successively, 1,000 parts by weight of boiled milk was gradually admixed with the resulting mixture and the resulting solution was continuously stirred on an open flame. The heating was stopped at the point that corn starch was completely gelatinized to give a transparency. After cooling the mixture, a suitable amount of vanilla essence was admixed with the mixture, weighted, and packed to make into a custard cream product. The product is a high quality custard cream with a satisfactory gloss and flavor, whose retrogradation of starch is inhibited.

EXAMPLE 14

Premix for "uiro"

Ninety parts by weight of rice powder, 20 parts by weight corn starch, 70 parts by weight of anhydrous crystalline maltitol, 50 parts by weight of a powder comprising CMM, obtained by the method in Example 5, and four parts by weight of pullulan were mixed to homogeneity to make into a premix for "uiro" (a Japanese rice cake). The premix for "uiro", a suitable amount of ground green tea and water was kneaded, put into a container, and steamed for 60 min to make into a "uiro" with ground green tea. The product has a satisfactory gloss, mouth feel, and flavor. Since the retrogradation of starch of the product is inhibited, the product keeps the quality well and is preferable as a "uiro" with a low calorie.

EXAMPLE 15

"An"

Bean Jam

According to conventional method, 10 parts by weight of "azuki" bean as material and water was mixed and boiled and the tannin, harshness, and water soluble components were removed, and then about 21 parts by weight of "tsubu-an" of "azuki" bean was obtained. To the row "an", 14 parts by weight of sucrose, five parts by weight of a syrup comprising CMM, obtained by the method in Example 2, and four parts by weight of water were mixed and the resulting mixture was boiled. The mixture was further admixed with a small amount of salad oil and kneaded without crushing the "tsubu-an" and about 35 parts by weight of "an" product was obtained. The product has a good stability with no browning and syneresis and shows a satisfactory mouthfeel and flavor. It can be preferably used as a material for confectionaries such as "an"-buns, "manju" (a Japanese bean-jam cake), "dango" (a Japanese rice cake), "monaka" (a Japanese bean-jam cake), "hyoka" (ice milk).

EXAMPLE 16

Bread

One hundred parts by weight of wheat flour, two parts by weight of yeast, five parts by weight of sucrose, one part by weight of a powder comprising CMM, obtained by the method in Example 3, 0.1 part by weight of mineral food and water was mixed and kneaded according to conventional method. The resulting dough was fermented at 26° C. for two hours, aged for 30 min, and then baked into bread. The product is bread with a high quality, satisfactory color and texture, adequate elasticity, and mild sweetness.

EXAMPLE 17

Ham

To 1,000 parts by weight of dark meat of pork, 15 parts by weight of sodium chloride and three parts by weight of potassium nitrate were penetrated and then preserved for one day in a refrigerated room. The resulting pork was soaked into a pickled solution composed of 500 parts by weight of water, 100 parts by weight of sodium chloride, three parts by weight of potassium nitrate, 40 parts by weight of a powder comprising CMM, obtained by the method in Example 5, and spices, for seven days in a refrigerated room. Successively, according to conventional method, the soaked pork was washed with cold water, rolled with a string, smoked, cooked, cooled and packed to make into a ham product. The product is a high-quality ham with a satisfactory color and flavor.

EXAMPLE 18

Powdery Peptide Product

To one part by weight of "HI-NUTE S", 40% soybean peptides solution for foods, commercialized by Fuji Oil Co., Ltd., Osaka, Japan, two parts by weight of powdery hydrous crystalline CMM, obtained by the method in Example 6, was mixed and the resulting mixture was put into a plastic tray, dried at 50° C. under a reduced pressure, and pulverized to make into a powdery peptide product. The product has a satisfactory flavor and is useful as a material for premix, low-calorie confectionaries for ice dessert. Further, the product is useful as a less-digestive dietary fiber and antiflaturent for a fluid diet for oral- or tube-intake.

EXAMPLE 19

Cosmetic Cream

According to conventional method, two parts by weight of polyoxiethylenglycol mono-stearate, five parts by weight of self-emulsified glycerin mono-stearate, two parts by weight of a powdery hydrous crystalline CMM, obtained by the method in Example 6, one part by weight of "αG-RUTIN", α-glucosyl rutin, commercialized by Hayashibara Inc., Okayama, Japan, one part by weight of liquid paraffin, 10 parts by weight of glycerin-trioctanoate and a suitable amount of preservative were mixed and dissolved by heating. The resulting mixture was further admixed with two parts by weight of lactic acid, five parts by weight of 1,3-butylen glycol, and 66 parts by weight of purified water, and the resulting mixture was emulsified using a homogenizer. The homogenized mixture was further admixed with a suitable amount of flavor and stirred to make into a cosmetic cream. The product has an antioxidative activity and satisfactory stability, and can be advantageously used as a sunburn preventive, skin-care agent and whitening agent for skin.

EXAMPLE 20

Toothpaste

Forty-five parts by weight of calcium monohydrogen phosphate, 1.5 parts by weight of sodium lauryl sulfate, 25 part by weight of glycerin, 0.5 part by weight of polyoxyethylene sorbitanlaurate, 10 parts by weight of a powder comprising CMM, obtained by the method in Example 5, 0.02 part by weight of saccharin, and 18 parts by weight of water were mixed to make into a toothpaste. The product is toothpaste whose bad taste is improved and shows a satisfactory availability without losing the washing property of surfactant.

EXAMPLE 21

Solid Agent for a Fluid Diet

One hundred parts by weight of a powder comprising CMM, obtained by the method in Example 3, 200 parts by weight of hydrous crystalline trehalose, 200 parts by weight of a maltotetraose high content powder, 270 parts by weight of powdery egg yolk, 209 parts by weight of skim milk, 4.4 parts by weight of sodium chloride, 1.8 parts by weight of potassium chloride, four parts by weight of magnesium sulfate, 0.01 part by weight of thiamine, 0.1 part by weight of sodium L-ascorbate, 0.6 parts by weight of vitamin E acetate, and 0.04 part by weight of nicotinic acid-amide were mixed to make into a composition. Twenty-five grams each of the composition was packed into a damp proof laminate pouch, and the pouch was heat-sealed to make into a product. Since the product is enriched with less-digestive dietary fiber by CMM, it can be advantageously used for supplying energy to living bodies as a fluid diet to regulate the function of intestine by taking orally or through tube into nasal cavity, stomach, and intestine.

EXAMPLE 22

Tablet

Fifty parts by weight of aspirin, 14 parts by weight of a powdery hydrous crystalline CMM, obtained by the method in Example 6, and four parts by weight of corn starch were mixed sufficiently. Then, according to conventional method, the mixture was shaped into a tablet with a sickness of 5.25 mm and 680 mg/tablet using a tablet machine. The product was prepared by applying the shaping ability of CMM. The product shows no hygroscopicity and has a satisfactory physical strength and decay property in water.

EXAMPLE 23

Ointment for Curing Wound

One hundred parts by weight of a powdery hydrous crystalline CMM, obtained by the method in Example 6, 300 parts by weight of maltose, and 50 parts by weight of a methanol solution containing three parts by weight of iodine, were mixed to make into an ointment for curing wound with an adequate extendability and adhesive property. Since the volatilization of iodine and methanol was prevented by CMM, the product is an ointment with a high marketability and less change over time. Since iodine in the product has an antimicrobial activity and maltose in the product acts as an energy-supplement for cells, the curing period is shortened and wound surface is cured completely.

INDUSTRIAL APPLICABILITY

According to the present invention, a novel cyclic saccharide having a structure of cyclo{>6)-α-D-lucopyranosyl-1>4)-α-D-glucopyranosyl-(1>6)-α-D-lucopyranosyl-(1>4)-α-D-glucopyranosyl-(1>}, which has been unknown, i.e., CMM can be provided in a large amount by producing the saccharide using CMM-forming enzyme. Since CMM is a non-reducing saccharide, it does not cause browning by reacting with amino compounds through amino-carbonyl reaction (Maillard reaction). Further, since CMM is a cyclic saccharide and has a clathrating activity, it can be used for inhibiting the volatilization of clathrated compounds and stabilizing them. The present invention, enabling to provide a novel cyclic maltosylmaltose, contributes to various fields such as foods and beverages, cosmetics, and pharmaceuticals. The present invention, having these outstanding functions and effects, is a significantly important invention that greatly contributes to this art.

What is claimed is:

1. A purified cyclic maltosylmaltose-forming enzyme which has an activity of forming a cyclic maltosylmaltose having a structure of cyclo{>6)-α-D-glucopyranosyl-(1>4)-α-D-glucopyranosyl-(1>6)-α-D-glucopyranosyl-(1>4)-α-D-glucopyranosyl-(1>} from α-1,4 glucan having a glucose polymerization degree of 3 or higher.

2. The purified cyclic maltosylmaltose-forming enzyme of claim 1, which has the following physicochemical properties:

(1) Molecular weight 72,000±20,000 daltons on SDS-PAGE;

(2) Isoelectric point pI 3.6±0.5 on isoelecrofocusing a carrier ampholyte;

(3) Optimum temperature 50-55° C. when reacted at pH 6.0 for 30 mm;

(4) Optimum pH 5.5 to 6.5 when reacted at 40° C. for 30 mm;

(5) Thermal stability

Stable up to the temperature of 30° C. when incubated at pH 6.0 for 60 mm;

Stable up to the temperature of 50° C. when incubated at pH 6.0 for 60 mm in the presence of 1 mM Ca2+ ion; and (6) pH Stability Stable in a range of pH 5.0 to 9.0 when incubated at 4° C. for 24 hours.

3. The purified cyclic maltosylmaltose-forming enzyme of claim 1, having an amino acid sequence of SEQ ID NO:1 as N-terminal amino acid sequence.

4. The purified cyclic maltosylmaltose-forming enzyme of claim 1, which has an amino acid sequence of SEQ ID NO:2 or an amino acid sequence having deletion, replacement, or addition of one or more amino acid residues of SEQ ID NO:2 without altering the enzyme activity.

5. The purified cyclic maltosylmaltose-forming enzyme of claim 1; wherein said α-1,4 glucan having a glucose polymerization degree of 3 or higher is one or more saccharides selected from the group consisting of maltooligosaccharide, maltodextrin, amylodextrin, amylose, amylopectin, soluble starch, liquefied starch, gelatinized starch and glycogen.

6. The purified cyclic maltosylmaltose-forming enzyme of claim 1, which is derived from a microorganism.

7. The purified cyclic maltosylmaltose-forming enzyme of claim 6, wherein said microorganism belongs to the genus *Arthrobacter*.

8. The purified cyclic maltosylmaltose-forming enzyme of claim 7, wherein said microorganism belonging to the genus *Arthrobacter* is *Arthrobacter globiformis* M6 (International Patent Organism Depository, National Institute of Advanced Industrial Science and Technology, Accession No. FERN BP-8448) or a mutant thereof.

9. A process for producing a cyclic maltosylmaltose-forming enzyme, comprising the steps of:

culturing a microorganism capable of producing the cyclic maltosylmaltose-forming enzyme of claim 1 in a nutrient culture medium; and collecting the cyclic maltosylmaltose-forming enzyme of claim 1 from the resulting culture.

10. The process of claim 9, wherein said microorganism belongs to the genus *Arthrobacter*.

11. The process of claim 10, wherein said microorganism belonging to the genus *Arthrobacter* is *Arthrobacter globiformis* M6 (International Patent Organism Depository, National Institute of Advanced Industrial Science and Technology, Accession No. FERM BP-8448) or a mutant thereof.

12. A method for forming a cyclic maltosylmaltose having a structure of cyclo{>6)-α-D-glucopyranosyl-(1>4)-α-D-lucopyranosyl(1>6)-α-D-glucopyranosyl-(1>4)-α-D-glucopyranosyl-(1>}, comprising a step of allowing the cyclic maltosylmaltose-forming enzyme of claim 1 to act on a solution containing α-1,4 glucan having a glucose polymerization degree of 3 or higher.

13. The method of claim 12, wherein said α-1,4 glucan having a glucose polymerization degree of 3 or higher is one or more saccharides selected from the group consisting of maltooligosaccharide, maltodextrin, amylodextrin, amylose, amylopectin, soluble starch, liquefied starch, gelatinized starch and glycogen.

14. A process for producing a cyclic maltosylmaltose product having a structure of cyclo{>6)-α-D-glucopyranosyl-(1>4)-α-D-glucopyranosyl-(1>6)-α-D-glucopyranosyl-(1>4)-α-D-glucopyranosyl-(1>}, comprising allowing the cyclic maltosylmaltose-forming enzyme of claim 1 to act on a solution obtained by gelatinizing and/or liquefying starch.

15. The process of claim 14, where the DE value of said solution obtained by gelatinizing and/or liquefying starch is 20 or lower.

16. The process of claim 14, comprising the steps of:

allowing said cyclicmaltosylmaltose-forming enzyme together with isoamylase to act on a solution obtained by gelatinizing and/or liquefying starch; and optionally, further allowing one or more enzymes selected from the group consisting of (α-amylase, β-amylase, cyclodextrin glucanotransferase, glucoamylase, and α-glucosidase, to act on the solution.

17. The process of claim 14, comprising the steps of:

allowing said cyclic maltosylmaltose-forming enzyme together with isoamylase to act on a solution obtained by gelatinizing and/or liquefying starch;

optionally, further allowing one or more enzymes selected from the group consisting of α-amylase, β-amylase, cyclodextrin glucanotransferase, glucoamylase, and (α-glucosidase, to act on the solution; and purifying the resultant mixture by one or more methods selected from the group consisting of fractionation by column chromatography, separation by membrane, fermentation by a microorganism, and elimination by alkaline treatment.

18. The process of claim 14, where the product comprises the cyclic maltosylmaltose in an amount of 1% (w/w) or higher, on a dry solid basis.

19. The process of claim 14, where the product is in the form of a syrup, massecuite, amorphous powder, amorphous solid, crystal, or crystalline solid.

* * * * *